(12) United States Patent
Iwata

(10) Patent No.: US 12,070,723 B2
(45) Date of Patent: Aug. 27, 2024

(54) MICROORGANISM RECOVERING METHOD AND MICROORGANISM RECOVERING APPARATUS

(71) Applicant: SHIMADZU CORPORATION, Kyoto (JP)

(72) Inventor: Hiroshi Iwata, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 654 days.

(21) Appl. No.: 17/071,274

(22) Filed: Oct. 15, 2020

(65) Prior Publication Data

US 2021/0113968 A1 Apr. 22, 2021

(30) Foreign Application Priority Data

Oct. 18, 2019 (JP) ................................ 2019-191186
Sep. 14, 2020 (JP) ................................ 2020-153761

(51) Int. Cl.
*B01D 63/08* (2006.01)
*B01D 61/18* (2006.01)
(Continued)

(52) U.S. Cl.
CPC .......... *B01D 63/087* (2013.01); *B01D 61/18* (2013.01); *B01D 61/58* (2013.01); *B01D 65/02* (2013.01);
(Continued)

(58) Field of Classification Search
CPC ...... B01D 63/087; B01D 61/18; B01D 61/58; B01D 65/02; B01D 2313/48;
(Continued)

(56) References Cited

U.S. PATENT DOCUMENTS 4,933,092 A    6/1990 Aunet et al.
2004/0185437 A1  9/2004 Hermet et al.
(Continued)

FOREIGN PATENT DOCUMENTS

JP    6-500403    1/1994
JP    10-215859   8/1998
(Continued)

OTHER PUBLICATIONS

Amy Fothergill et al., "Rapid Identification of Bacteria and Yeasts from Positive-Blood-Culture Bottles by Using a Lysis-Filtration Method and Matrix-Assisted Laser Desorption Ionization-Time of Flight Mass Spectrum Analysis with the SARAMIS Database", Journal of Clinical Microbiology, vol. 51, No. 3, p. 805-809, Mar. 2013.

(Continued)

*Primary Examiner* — Michael L Hobbs
*Assistant Examiner* — Lenora A Abel
(74) *Attorney, Agent, or Firm* — Wenderoth, Lind & Ponack, L.L.P.

(57) ABSTRACT

A microorganism recovering method high in recovering efficiency is provided. A microorganism recovering method of recovering microorganisms from a liquid sample includes filtering out microorganisms from the liquid sample through a filtration apparatus, the filtration apparatus including a first end and a second end, the filtration apparatus being configured to receive the liquid sample at the first end and being configured to discharge from the second end filtrate generated through the filtering out microorganisms and recovering the microorganisms filtered out by the filtration apparatus together with a culture medium by feeding the culture medium from the second end to the first end.

8 Claims, 14 Drawing Sheets

(51) Int. Cl.
*B01D 61/58* (2006.01)
*B01D 65/02* (2006.01)
*C12M 1/26* (2006.01)
*C12N 1/02* (2006.01)

(52) U.S. Cl.
CPC .............. *C12M 33/14* (2013.01); *C12N 1/02* (2013.01); *B01D 2313/48* (2013.01); *B01D 2313/50* (2013.01); *B01D 2317/08* (2013.01); *B01D 2321/168* (2013.01)

(58) Field of Classification Search
CPC ........... B01D 2313/50; B01D 2317/08; B01D 2321/168; C12M 33/14; C12N 1/02
USPC ........................................... 435/308.1, 287.2
See application file for complete search history.

(56) References Cited

U.S. PATENT DOCUMENTS

| | | | |
|---|---|---|---|
| 2007/0298451 | A1 | 12/2007 | Ribault et al. |
| 2012/0088227 | A1 | 4/2012 | Gruebl et al. |
| 2016/0251628 | A1* | 9/2016 | Vincent ............... B01D 63/087 424/93.7 |
| 2017/0191114 | A1 | 7/2017 | Kamba et al. |
| 2020/0046891 | A1 | 2/2020 | Yamashita et al. |
| 2021/0113968 | A1 | 4/2021 | Iwata |
| 2021/0116337 | A1 | 4/2021 | Iwata |

FOREIGN PATENT DOCUMENTS

| | | |
|---|---|---|
| JP | 2003-194806 | 7/2003 |
| JP | 2005-503803 | 2/2005 |
| JP | 2006-262891 | 10/2006 |
| JP | 2014-117220 | 6/2014 |
| JP | 2015-216875 | 12/2015 |
| WO | 92/17110 | 10/1992 |
| WO | 2016/194463 | 12/2016 |
| WO | 2018/194061 | 10/2018 |
| WO | 2019/163452 | 8/2019 |

OTHER PUBLICATIONS

Office Action issued May 30, 2023 in related U.S. Appl. No. 17/069,043.
Concise Medical Dictionary, 2014, Oxford University Press, 8th edition, definition of 'microorganism'.
Notice of Reasons for Refusal issued Jul. 25, 2023 in Japanese Patent Application No. 2019-191185, with English language translation.
Notice of Reasons for Refusal issued Dec. 26, 2023 in corresponding Japanese Patent Application No. 2020-153761 with English translation.
Notice of First Examination Opinion issued Jan. 22, 2024 in corresponding Chinese Patent Application No. 202011097284.2 with English translation.
Decision of Refusal issued Feb. 6, 2024 in Japanese Patent Application No. 2019-191185 with English translation.
U.S. Appl. No. 17/721,572, filed Apr. 15, 2022.
Martin Christner et al., "Rapid Identification of Bacteria from Positive Blood Culture Bottles by Use of Matrix-Assisted Laser Desorption-Ionization Time of Flight Mass Spectrometry Fingerprinting", Journal of Clinical Microbiology 48(5), pp. 1584-1591, May 2010.
S. Deponte et al., "Biomagnetic separation of *Escherichia coli* by use of anion-exchange beads: Measurement and modeling of the kinetics of cell-bead interactions", Analytical and Bioanalytical Chemistry 379, pp. 419-426, Jun. 2004.
Notice of Reasons for Refusal issued Dec. 20, 2022 in Japanese Patent Application No. 2019-191185, with English language translation.
Office Action issued Dec. 20, 2022 in U.S. Appl. No. 17/069,043.
Office Action issued Oct. 5, 2022, in U.S. Appl. No. 17/069,043.

* cited by examiner

MICROORGANISM RECOVERING METHOD AND MICROORGANISM RECOVERING APPARATUS

BACKGROUND OF THE INVENTION

Field of the Invention

The present invention relates to a microorganism recovering method and a microorganism recovering apparatus.

Description of the Background Art

In identifying microorganisms such as bacteria contained in blood, a method of removing a blood cell component which interferes measurement, recovering microorganisms, and culturing the recovered microorganisms has been known. For example, Amy Fothergill, Vyjayanti Kasinathan, Jay Hyman, John Walsh, Tim Drake, and Yun F. (Wayne) Wang, Journal of Clinical Microbiology, 51, 805-809 (2013) discloses a method of recovering bacteria in a blood culture broth by adding a cell lysis solution to the blood culture broth to lyse cell membranes of blood cells, thereafter filtering the broth through a filter, and removing a substance recovered on the filter with a microswab applicator.

SUMMARY OF THE INVENTION

The method of removing a substance on a filter surface with a microswab applicator disclosed above requires a manual operation to remove microorganisms with the microswab applicator and is not suitable for automation.

The present invention was made to solve such a problem, and an object thereof is to provide a microorganism recovering method and a microorganism recovering apparatus that allow automated recovering of microorganisms.

A microorganism recovering method according to the present disclosure includes filtering out microorganisms from a liquid sample through a filtration apparatus, the filtration apparatus including a first end and a second end, the filtration apparatus being configured to receive the liquid sample at the first end and being configured to discharge from the second end filtrate generated through the filtering out microorganisms and recovering the microorganisms filtered out by the filtration apparatus together with recovering fluid by feeding the recovering fluid from the second end to the first end.

Since the microorganism recovering method allows separation and recovering of microorganisms from the filtration apparatus by force of flow of recovering fluid, it allows automated recovering of microorganisms.

A microorganism recovering apparatus according to the present disclosure includes a sample container that receives a liquid sample, a filtration apparatus including a filter having a pore size smaller than microorganisms and a first opening and a second opening formed at positions opposed to each other with the filter being interposed, a waste fluid container that receives waste fluid, a recovering fluid container that receives recovering fluid, a recovering container that receives a solution to be recovered, a first flow path through which the sample container is connected to a side of the first opening of the filtration apparatus and the waste fluid container is connected to a side of the second opening of the filtration apparatus, and a second flow path through which the recovering fluid container is connected to a side of the second opening of the filtration apparatus and the recovering container is connected to the side of the first opening of the filtration apparatus.

The microorganism recovering apparatus can recover microorganisms filtered out by the filtration apparatus together with recovering fluid by filtering out the microorganisms through the filtration apparatus by feeding the liquid sample from the sample container and thereafter feeding recovering fluid toward the filtration apparatus. Therefore, by using the microorganism recovering apparatus, microorganisms can be separated and recovered from the filtration apparatus with force of flow of the recovering fluid and the microorganisms can be recovered without a manual operation. Therefore, automated recovering of microorganisms is allowed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
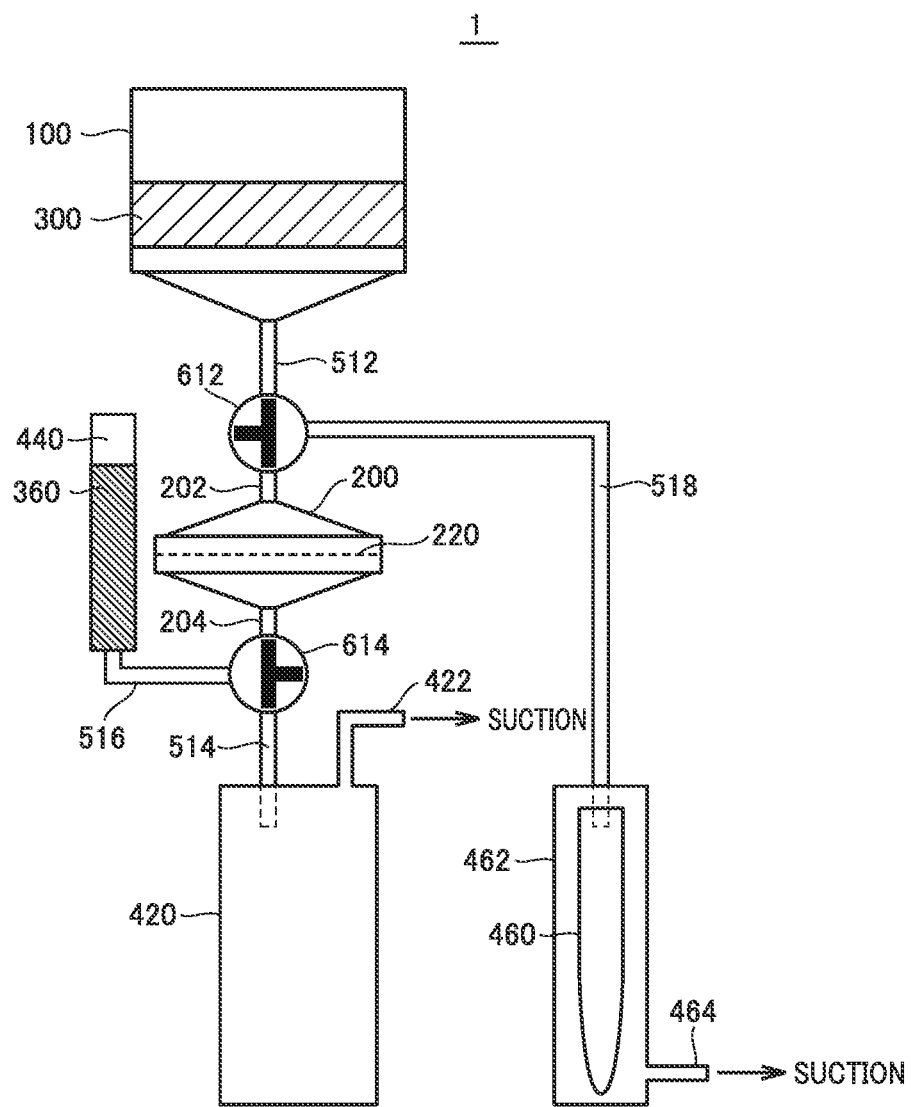
FIG. 1 is a diagram schematically showing an overall configuration of a recovering apparatus according to a first embodiment.

An embodiment of the present disclosure will be described below in detail with reference to the drawings. The same or corresponding elements in the drawings have the same reference characters allotted and description thereof will not be repeated. Hatching in the drawings represents a liquid component.

A recovering apparatus according to the present disclosure is used, for example, for a pretreatment step in identifying microorganisms in blood. The recovering apparatus according to the present disclosure is an apparatus for filtering a liquid sample by full amount (dead-end) filtration. The recovering apparatus according to the present disclosure is preferably disposable in consideration of its object to obtain microorganisms in blood. Microorganisms to be recovered in the present disclosure include, for example, bacteria such as germs and fungi, viruses, and molds.

[First Embodiment]

<Configuration of Recovering Apparatus>

FIG. 1 is a diagram schematically showing an overall configuration of a recovering apparatus according to a first embodiment. A recovering apparatus 1 includes a sample container 100 that receives a liquid sample 300, a filtration apparatus 200, a waste fluid container 420 that receives filtrate (waste fluid) resulting from filtration of liquid sample 300 through filtration apparatus 200, a culture medium container 440 that receives a culture medium 360, a recovering container 460 where microorganisms 340 are recovered, a first switch 612, and a second switch 614.

Filtration apparatus 200 includes a catch filter 220 including pores smaller in diameter than a microorganism. In filtration apparatus 200, an inlet port 202 and an outlet port 204 are formed at positions opposed to each other with catch filter 220 being interposed. First switch 612 is connected to inlet port 202. Second switch 614 is connected to outlet port 204.

A sample path 512 that extends to sample container 100 and a recovering path 518 that extends to recovering container 460 are connected to first switch 612, in addition to inlet port 202. By operating first switch 612, a flow path in fluid connection to inlet port 202 of filtration apparatus 200 can be switched to sample path 512 or recovering path 518.

A waste fluid path 514 that extends to waste fluid container 420 and a culture medium path 516 that extends to culture medium container 440 are connected to second switch 614, in addition to outlet port 204. By operating second switch 614, a flow path in fluid connection to outlet port 204 of filtration apparatus 200 can be switched to waste fluid path 514 or culture medium path 516.

For example, a three-way turncock is adopted as first switch 612 and second switch 614. First switch 612 and second switch 614 may be a switch requiring a manual operation or an electrical switch.

Catch filter 220 is designed in accordance with the size of a microorganism to be recovered. Catch filter 220 may be a filter for surface filtration or a filter for depth filtration as long as it can filter out a microorganism to be recovered. When a filter for surface filtration is adopted as catch filter 220, microorganisms are collected on catch filter 220, and on the other hand, when a filter for depth filtration is adopted as catch filter 220, microorganisms are captured inside the filter. Therefore, when a filter for surface filtration is adopted as catch filter 220, it is expected that microorganisms may be recovered more easily than the case when a filter for depth filtration is adopted.

When microorganisms to be recovered are bacteria, catch filter 220 is, for example, a general sterilization filter having a nominal pore size of 0.2 to 3.00 μm.

For example, as liquid sample 300 is fed from inlet port 202 toward outlet port 204, catch filter 220 can filter out microorganisms from liquid sample 300.

Recovering container 460 is provided in a suction box 462. A suction portion 464 is provided in a side surface of suction box 462. Though not shown, a vacuum pump is connected to suction portion 464 through a tube. By driving the vacuum pump, a pressure in suction box 462 can be reduced. For example, it is assumed that first switch 612 is operated to connect inlet port 202 and recovering path 518 to each other and second switch 614 is operated to connect outlet port 204 and culture medium path 516 to each other. When a pressure in suction box 462 is reduced in this state, culture medium 360 flows through culture medium path 516 into filtration apparatus 200. Culture medium 360 that has flowed into filtration apparatus 200 flows toward inlet port 202 from outlet port 204, is discharged from inlet port 202, and flows toward recovering path 518.

A suction portion 422 is provided above waste fluid container 420. Though not shown, a vacuum pump is connected to suction portion 422 through a tube. By driving the vacuum pump, a pressure in waste fluid container 420 can be reduced. For example, it is assumed that liquid sample 300 is set in sample container 100, first switch 612 is operated to connect inlet port 202 and sample path 512 to each other, and second switch 614 is operated to connect outlet port 204 and waste fluid path 514 to each other. When a pressure in waste fluid container 420 is reduced in this state, liquid sample 300 flows through sample path 512 into filtration apparatus 200. Liquid sample 300 that has flowed into filtration apparatus 200 flows from inlet port 202 toward outlet port 204, is discharged from outlet port 204, and flows toward waste fluid container 420. Liquid sample 300 is thus filtered out by catch filter 220 and filtrate is collected as waste fluid in waste fluid container 420. Assuming that the end a side of inlet port 202 of filtration apparatus 200 is a first end and the end a side of outlet port 204 of filtration apparatus 200 is a second end, liquid sample 300 is received at the first end and filtrate is discharged from the second end. In other words, filtration apparatus 200 includes the first end where liquid sample 300 flows in and the second end where filtrate is discharged.

In the first embodiment, a flow path formed by connection of sample path 512 and inlet port 202 to each other with first switch 612 being interposed for a flow of fluid and connection of outlet port 204 and waste fluid path 514 to each other with second switch 614 being interposed for a flow of fluid corresponds to the "first flow path."

A flow path formed by connection of recovering path 518 and inlet port 202 to each other with first switch 612 being interposed for a flow of fluid and connection of outlet port 204 and culture medium path 516 to each other with second switch 614 being interposed for a flow of fluid corresponds to the "second flow path."

By operating first switch 612 and second switch 614, a flow path formed in recovering apparatus 1 can be switched to the first flow path or the second flow path.

<Recovering Method>

Figure 2:
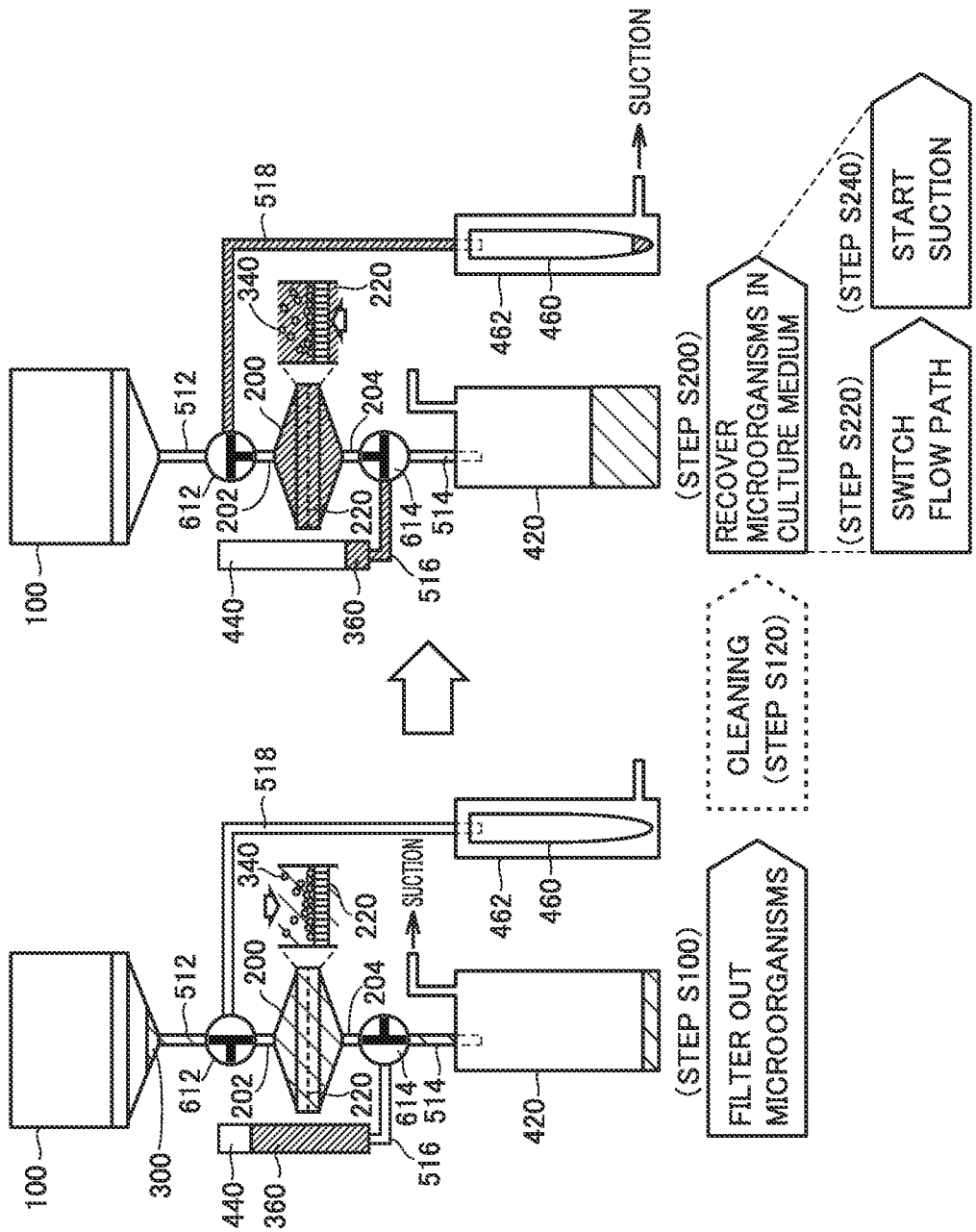
FIG. 2 is a diagram showing overview of a flow of a microorganism recovering method using the recovering apparatus according to the first embodiment.

A microorganism recovering method using recovering apparatus 1 according to the first embodiment will be described. FIG. 2 is a diagram showing overview of a flow of a microorganism recovering method using the recovering apparatus according to the first embodiment. A white circle labeled with a reference numeral 340 in FIG. 2 represents microorganism 340.

Liquid sample 300 of interest in the first embodiment is, for example, a sample of blood taken from a patient and cultured, from which blood cells have been removed. In general, approximately 8 ml to 10 ml of blood is taken from a patient for culturing blood. Liquid sample 300 employed in the first embodiment is obtained by culturing blood taken from a patient and thereafter removing blood cells by performing an appropriate operation such as centrifugation or filtration through a membrane onto cultured blood. Liquid sample 300 may be prepared by adding a lysing solution for lysis of cell membranes of blood cells to cultured blood. In other words, liquid sample 300 of interest in the first embodiment should only be treated such that a substance that interferes a test (measurement) conducted by recovering microorganisms 340 is not filtered out together with microorganisms 340 during filtration through filtration apparatus 200.

Initially, a step S100 of filtering out microorganisms 340 from liquid sample 300 is performed. Specifically, when the vacuum pump is driven to reduce a pressure in waste fluid container 420 while sample path 512 and waste fluid path 514 are connected to filtration apparatus 200, liquid sample 300 is suctioned and filtered to filter out microorganisms 340 from liquid sample 300.

Then, a step S200 of recovering together with culture medium 360, microorganisms 340 filtered out through filtration apparatus 200 is performed. Culture medium 360 is a liquid culture medium to be used for culturing microorganisms 340. Culture medium 360 is selected in accordance with a type of a microorganism to be recovered, and for example, Mueller-Hinton agar is adopted.

Step S200 includes a step S220 of switching a flow path and a step S240 of starting suction. In step S220, first switch 612 is operated to switch the flow path to be connected to filtration apparatus 200 from sample path 512 to recovering path 518, and second switch 614 is operated to switch the flow path to be connected to filtration apparatus 200 from waste fluid path 514 to culture medium path 516. That is, in step S220, a flow path connected to the first end on the side of inlet port 202 switches to recovering path 518, and a flow path connected to the second end on the side of outlet port 204 switches to culture medium path 516.

Step S240 is performed after step S220. In step S240, the vacuum pump is driven to reduce a pressure in suction box 462. Culture medium 360 thus passes through outlet port 204 of filtration apparatus 200 from culture medium path 516, is discharged from inlet port 202, passes through recovering path 518, and is received in recovering container 460. That is, in step S240, culture medium 360 is fed from the second end on the side of outlet port 204 to the first end on the side of inlet port 202.

As culture medium 360 flows from a side of outlet port 204 toward inlet port 202 in filtration apparatus 200, microorganisms 340 that have been filtered out on catch filter 220 in step S100 pass through recovering path 518 along the flow of culture medium 360 and are recovered in recovering container 460.

As set forth above, according to the microorganism recovering method in the first embodiment, microorganisms 340 are separated and recovered from catch filter 220 with force of flow of culture medium 360, instead of recovering by a manual operation. Therefore, the microorganism recovering method according to the first embodiment allows automated recovering of microorganisms. According to the microorganism recovering method in the first embodiment, microorganisms can be recovered without a manual operation, and hence contamination is less likely. In an example where a microorganism is a pathogen, infection can be prevented.

When microorganisms 340 are recovered by using recovering apparatus 1 according to the first embodiment, microorganisms 340 filtered out through filtration apparatus 200 are directly recovered in culture medium 360, and hence efficiency in recovering microorganisms 340 can be enhanced.

Furthermore, according to the microorganism recovering method in the first embodiment, by feeding culture medium 360 from the side of outlet port 204 toward inlet port 202, microorganisms 340 that clog pores in catch filter 220 can be flushed by culture medium 360. Therefore, not only microorganisms 340 on catch filter 220 but also microorganisms 340 that clog catch filter 220 can be recovered.

By thus enhancing efficiency in recovering microorganisms, time required for culturing the recovered microorganisms to a prescribed number of microorganisms can be shortened.

A cleaning step S120 may be performed between step S100 and step S200. In step S120, for example, filtration apparatus 200 is cleaned by introducing a cleaning solution into sample container 100 and reducing a pressure in waste fluid container 420, without switching a flow path after step S100. The cleaning solution is a buffer or the like adjusted to pH at which microorganisms 340 to be recovered are not killed, and examples thereof include a 20 mM sodium phosphate buffer adjusted to pH 7.2.

By thus performing step S120 of cleaning filtration apparatus 200, a substance smaller than microorganism 340 attached to the inside of inlet port 202, catch filter 220, and the inside of outlet port 204 or a substance that clogs a gap between microorganisms 340 deposited on catch filter 220 can be removed by cleaning. Consequently, such a substance can be prevented from being mixed at the time when culture medium 360 is fed, and microorganisms 340 can be recovered with high purity.

[Second Embodiment]

<Configuration of Recovering Apparatus>

Figure 3:
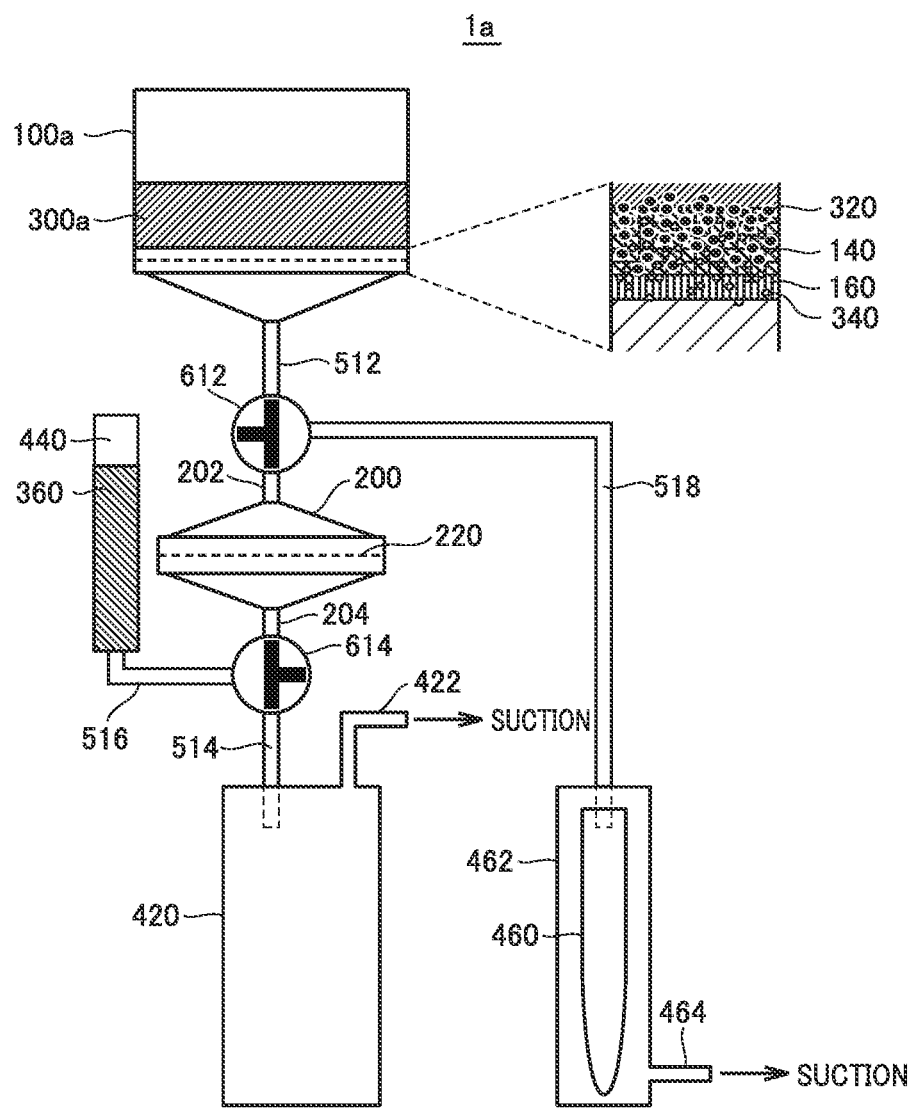
FIG. 3 is a diagram schematically showing an overall configuration of a recovering apparatus according to a second embodiment.

FIG. 3 is a diagram schematically showing an overall configuration of a recovering apparatus according to a second embodiment. A recovering apparatus 1 a according to the second embodiment is different from recovering apparatus 1 according to the first embodiment in including a blood cell removal apparatus 100a instead of sample container 100. Differences of recovering apparatus 1 a from recovering apparatus 1 will mainly be described below. A black circle labeled with a reference numeral 320 in FIG. 3 represents a blood cell.

Blood cell removal apparatus 100a includes therein, a first filter 140 and a second filter 160 at the bottom thereof. Second filter 160 is provided on the downstream of first filter 140 (a side where sample path 512 is connected). First filter 140 is stacked on second filter 160. Therefore, when sucked from the side of sample path 512, first filter 140 is in close contact with second filter 160.

First filter 140 is configured to permeate blood cells and components smaller than the blood cells. When a liquid sample such as whole blood containing blood cells and microorganisms to be recovered smaller than the blood cells is filtered by first filter 140, microorganisms pass through first filter 140 faster than the blood cells. At least some of microorganisms may pass through first filter 140 faster than the blood cells and some of the blood cells may pass through first filter 140 faster than some of microorganisms.

First filter 140 may be a filter for surface filtration or a filter for depth filtration as long as first filter 140 is capable of permeating blood cells and components smaller than the blood cells and advancing microorganisms faster than the blood cells.

First filter 140 includes a mechanism that three-dimensionally and temporarily captures blood cells. As an example of a filter including a mechanism that temporarily captures blood cells, a filter for depth filtration may specifically be given. Even though first filter 140 may capture three-dimensionally and temporarily the blood cells, first filter 140 has a path having a diameter sufficient to allow the blood cells to pass through when a pressure is continuously applied to the blood cells.

The components of blood cells are mainly composed of white blood cells and red blood cells. White blood cells are relatively large particles having a particle size of about 10 to 15 µm. Red blood cells have a particle size of about 7 to 8 µm. The number of red blood cells is greater than that of white blood cells in blood. Therefore, it is preferable that the path of first filter 140 has a diameter such that at least the red blood cells are allowed to pass through while being captured three-dimensionally and temporarily. Specifically, first filter 140 has a path having a diameter of at least 7 µm. From another viewpoint, first filter 140 has a particle retention capacity of 2.7 µm.

It should be noted that first filter 140 may include pores each having a diameter such that platelets having a particle size of about 2 µm contained in blood may be captured three-dimensionally and temporarily.

The filter for depth filtration may be, for example, a depth filter obtained by pressing a fibrous material or a porous membrane having a porous structure.

First filter 140 may be made of any material such as glass, resin, metal, or ceramics. Considering the fact that blood cells are adsorbed in the path and thereby the path may be blocked by the adsorbed blood cells, first filter 140 may be made of such a material that the adsorbed blood cells may be desorbed therefrom. For example, first filter 140 is a glass fiber filter or a cellulose filter.

Second filter 160 selectively captures blood cells by size and selectively permeates microorganisms by size. Specifically, second filter 160 has a pore size smaller than the blood cells and larger than microorganisms. For example, second filter 160 is configured to have a pore size capable of removing at least those components equal to or larger than red blood cells in the blood cells, and the pore size may be, for example, 2 µm or more and 6 µm or less. The expression that "the blood cells are selectively captured by size and microorganisms are selectively permeated by size" means that the blood cells are captured in the pores of the filter material, whereas microorganisms are permeated without being captured in the pores of the filter material. Alternatively, microorganisms may be temporarily captured when microorganisms are made to move straightly by the inertial force and collide with the filter material.

Second filter 160 may be a filter for surface filtration or a filter for depth filtration as long as it can remove blood cells. When a filter for surface filtration is used as second filter 160, it is possible to reliably remove blood cells as compared with the case where a filter for depth filtration is used, which makes it possible to reduce the possibility that the blood cells are mixed in the filtrate.

As an example material of second filter 160, polyethersulfone, cellulose mixed ester, cellulose acetate, nitrocellulose, polytetrafluoroethylene (PTFE), polyvinylidene fluoride (PVDF), polycarbonate or the like may be given.

<Recovering Method>

Figure 4:
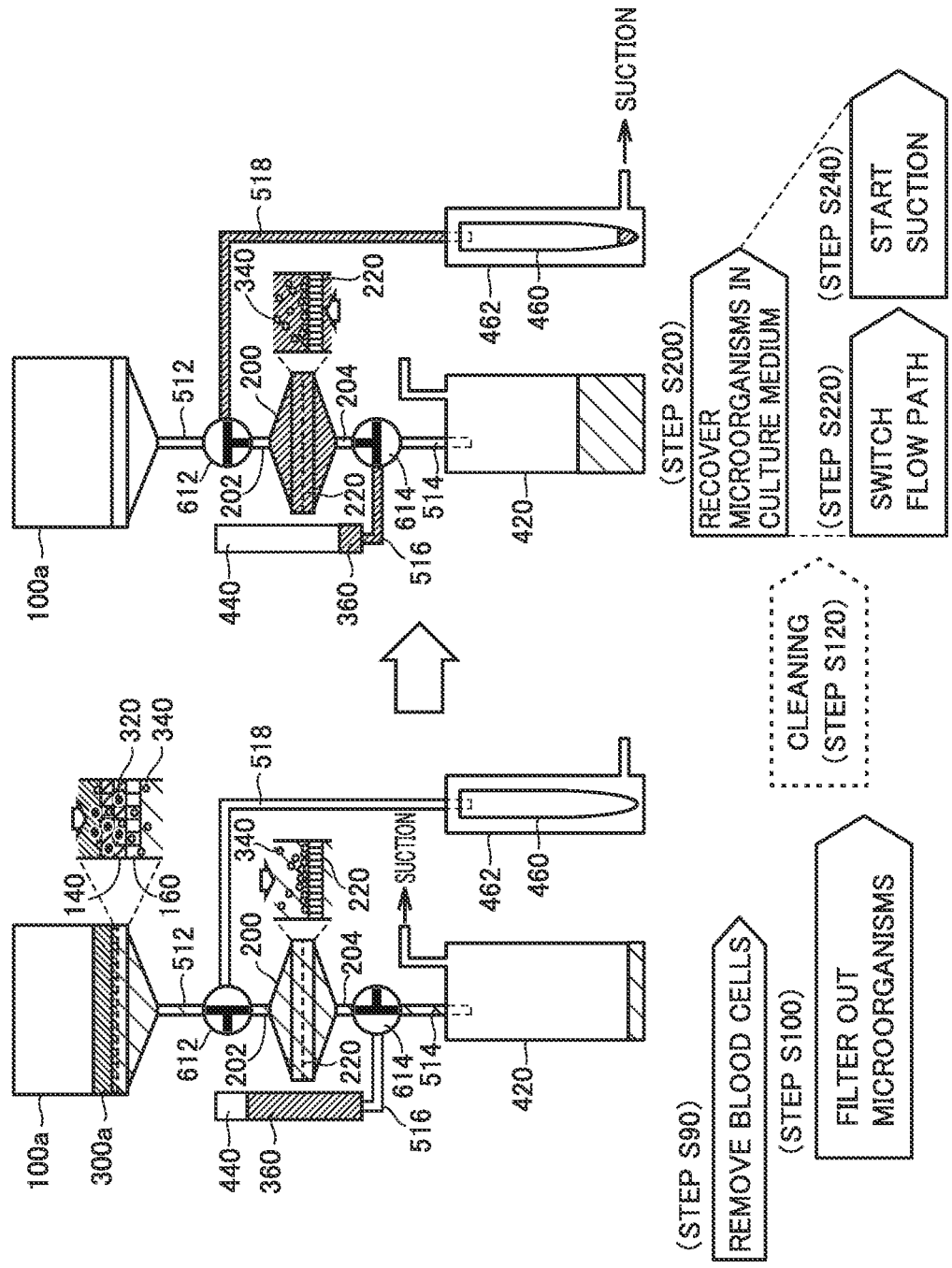
FIG. 4 is a diagram showing overview of a flow of a microorganism recovering method using the recovering apparatus according to the second embodiment.

A microorganism recovering method using recovering apparatus 1*a* according to the second embodiment will be described. FIG. 4 is a diagram showing overview of a flow of a microorganism recovering method using the recovering apparatus according to the second embodiment.

The microorganism recovering method using recovering apparatus 1*a* according to the second embodiment is different from the microorganism recovering method (see FIG. 2) using recovering apparatus 1 according to the first embodiment in including a step S90 of removing blood cells.

First switch 612 and second switch 614 are operated to connect sample path 512 and waste fluid path 514 to filtration apparatus 200. As a pressure in waste fluid container 420 is reduced by driving the vacuum pump in this state, a liquid sample 300*a* is suctioned and filtered and treated in the order of steps S90 and S100.

After treatment in step S100, as in the microorganism recovering method using recovering apparatus 1 according to the first embodiment, treatment in the order of step S220 of switching a flow path and step S240 of starting suction is performed and microorganisms 340 filtered out by filtration apparatus 200 are recovered together with culture medium 360 (S200).

Since recovering apparatus 1*a* includes blood cell removal apparatus 100*a*, blood cells 320 which interfere a test (measurement) conducted by recovering microorganisms 340 can be removed out of liquid sample 300*a* in blood cell removal apparatus 100*a*. Therefore, recovering apparatus 1*a* according to the second embodiment can treat blood taken from a patient as it is. Consequently, by making use of recovering apparatus 1*a* according to the second embodiment, a pretreatment step such as treatment for removing blood cells or treatment for lysing blood cells does not have to be performed.

Cleaning step S120 may be performed between steps S100 and S200 also in the microorganism recovering method using recovering apparatus 1*a*, as in the microorganism recovering method using recovering apparatus 1.

<Blood Cell Removal Method>

Figure 5:
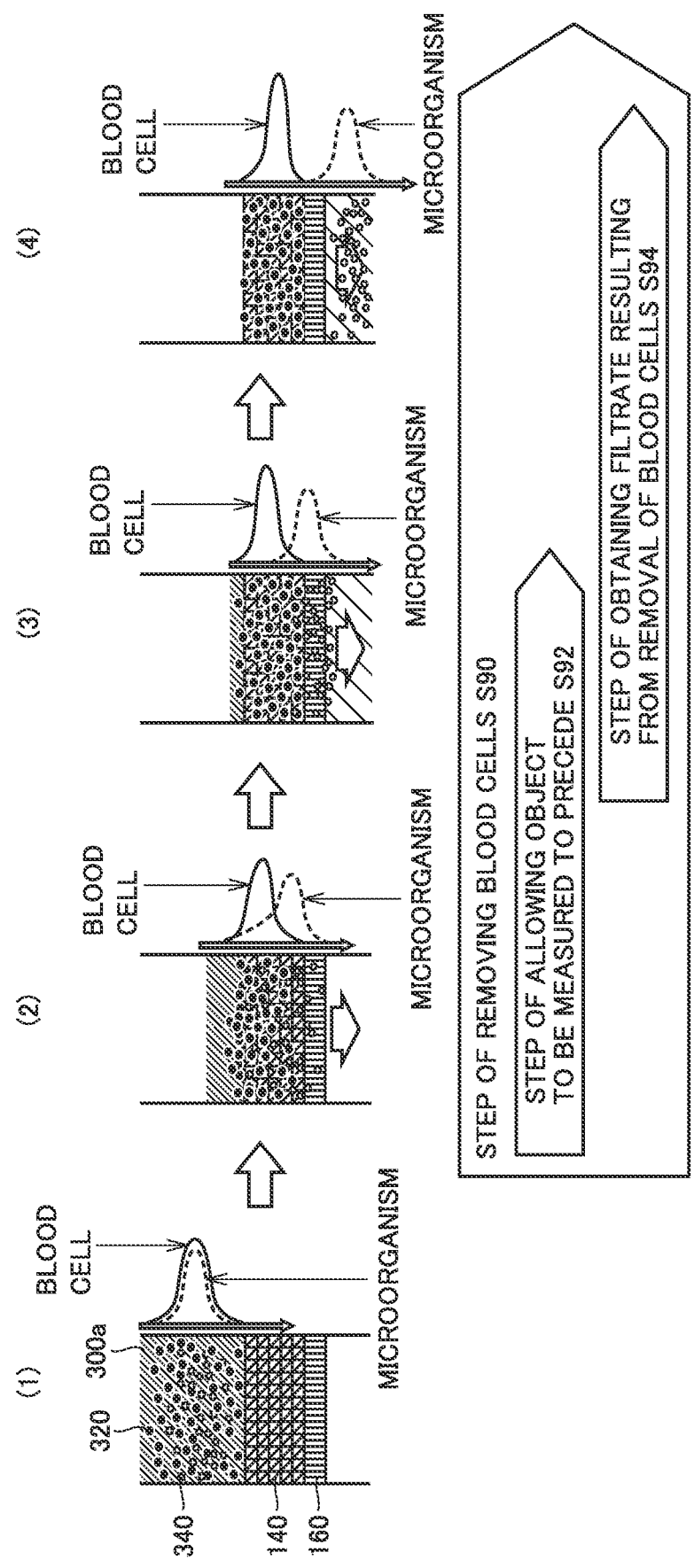
FIG. 5 is a diagram schematically illustrating the movement of blood cells and microorganisms when a liquid sample is filtered by a first filter and a second filter in a blood cell removal apparatus according to the second embodiment.

A method of removing blood cells (step S90 of removing blood cells) using a blood cell removal apparatus will be described with reference to FIG. 5. FIG. 5 is a diagram schematically illustrating the movement of blood cells and microorganisms when a liquid sample is filtered by a first filter and a second filter in the blood cell removal apparatus according to the second embodiment.

In FIG. 5, it is assumed that a liquid sample 300*a* which contains blood cells 320 and microorganisms 340 is filtered. The size of microorganisms 340 is smaller than that of blood cells 320. If the microorganisms are bacteria, the size of microorganisms 340 is about 1 µm.

Liquid sample 300*a* containing blood cells 320 and microorganisms 340 is, for example, blood collected from a patient and cultured thereafter. Liquid sample 300*a* may be blood diluted with another solution.

The graph in FIG. 5 illustrates an example concentration distribution in the thickness direction of the membrane (first filter 140 and second filter 160). The solid line in the graph illustrates the concentration distribution of blood cells, and the broken line in the graph illustrates the concentration distribution of microorganisms. Some of reference numerals are not shown in FIG. 5.

Phase (1) in FIG. 5 illustrates a state before filtration, phase (2) and phase (3) in FIG. 5 illustrate states during filtration, and phase (4) in FIG. 5 illustrates a state after filtration. Specifically, when liquid sample 300*a* is filtered by blood cell removal apparatus 100*a*, the state inside blood cell removal apparatus 100*a* changes over time in the order of phase (1) to phase (4) as illustrated in FIG. 5.

As illustrated in phase (1) of FIG. 5, before filtration, both blood cells 320 and microorganisms 340 are dispersed in liquid sample 300a.

When liquid sample 300a is filtered by suction, liquid sample 300a first passes through first filter 140. At this time, blood cells 320 collide with the filter material in the path of first filter 140 and are temporarily captured. In contrast, microorganisms 340 smaller than blood cells 320 are less likely to be temporarily captured in the path of first filter 140 than blood cells 320. Therefore, in the first filtration using first filter 140, the filtration resistance against microorganisms 340 is smaller than the filtration resistance against blood cells 320. In other words, the filtration resistance of first filter 140 against microorganisms 340 is smaller than the filtration resistance of first filter 140 against blood cells 320. As a result, as illustrated in phase (2) and phase (3) of FIG. 5, as the time elapses, blood cells 320 and microorganisms 340 in liquid sample 300a are gradually separated from each other, and microorganisms 340 generally pass through the first filter faster than blood cells 320 in the moving direction of liquid sample 300a.

As illustrated in phase (3) of FIG. 5, since first filter 140 is stacked on second filter 160, and after liquid sample 300a is filtered by first filter 140, microorganisms 340 generally pass through the first filter faster than blood cells 320 in the moving direction of liquid sample 300a, and thereby, microorganisms 340 reach second filter 160 earlier than blood cells 320.

Since microorganisms 340 generally pass through the first filter faster than blood cells 320 in the moving direction of liquid sample 300a, blood cells 320 are retained on first filter 140, and liquid sample 300a is subjected to the second filtration using second filter 160 so as to selectively permeate microorganisms 340 by size, which makes it possible to obtain a filtrate which contains microorganisms 340 and from which blood cells 320 are removed, as illustrated in phase (4) of FIG. 5.

As described above, the step (S90) of removing blood cells is realized by filtering liquid sample 300a using blood cell removal apparatus 100a. The step (S90) of removing blood cells includes a step (S92) of performing a first filtration on liquid sample 300a by using first filter 140 which has a filtration resistance against microorganisms 340 smaller than the filtration resistance against blood cells 320, microorganisms 340 generally passing through the first filter faster than blood cells 320, and a step (S94) of performing a second filtration while blood cells 320 are retained on first filter 140 by using second filter 160 to selectively permeate microorganisms 340 by size so as to obtain a final filtrate from which blood cells 320 are removed out of the liquid sample.

When first filter 140 is a filter for depth filtration such as a depth filter, the first filtration is depth filtration. When second filter 160 is a filter for surface filtration such as a membrane filter, the second filtration is surface filtration.

When a liquid sample such as blood is filtered by second filter 160 without using first filter 140, blood cells 320 may be accumulated on second filter 160 and clog second filter 160 before microorganisms 340 pass through second filter 160. Therefore, when a liquid sample such as blood is filtered only by second filter 160, the recovery efficiency of microorganisms 340 is low.

Liquid sample 300a is filtered by first filter 140, which makes it possible for microorganisms 340 to pass through the first filter faster than blood cells 320 in the moving direction of liquid sample 300a. Since microorganisms 340 pass through the first filter faster than blood cells 320 in the moving direction of liquid sample 300a, when liquid sample 300a is filtered by second filter 160, microorganisms 340 pass through second filter 160 before blood cells 320 are accumulated on second filter 160 and clog second filter 160. As a result, it is possible to remove blood cells 320 out of liquid sample 300a and efficiently recover microorganisms 340.

The thickness of first filter 140 is designed according to, for example, the difference between the permeation rate of blood cells 320 passing through the membrane and the permeation rate of microorganisms 340 passing through the membrane, and may be any thickness as long as blood cells 320 are accumulated on second filter 160 after microorganisms 340 has passed through second filter 160 so as to separate blood cells 320 and microorganisms 340 from each other. For example, first filter 140 may have a thickness of 1.3 mm or more.

The blood cell removal apparatus may be configured such that blood cells 320 do not reach second filter 160 or such that all or some of blood cells 320 reach second filter 160 at the time when the full amount of liquid sample 300a has been filtered. The first filtration may be conducted on liquid sample 300a by using first filter 140, whereby microorganisms 340 generally pass through the first filter faster than blood cells 320, and thereafter, microorganisms 340 may be selectively permeated by size in the second filtration, whereby the filtrate out of which the blood cells have been removed can be obtained without causing clogging.

As set forth above, in recovering apparatus 1a according to the second embodiment, microorganisms 340 pass through second filter 160 before blood cells 320. Therefore, microorganisms 340 can pass before blood cells 320 clog second filter 160 and microorganisms can efficiently be left in filtrate. In recovering apparatus 1a, while microorganisms are efficiently left in filtrate, microorganisms 340 are filtered out through filtration apparatus 200 from the filtrate and the filtered-out microorganisms are directly recovered in culture medium 360. Therefore, efficiency in recovering microorganisms 340 can be improved. By thus improving efficiency in recovering microorganisms, time required for culturing recovered microorganisms and growing them to a prescribed number can be shortened.

[Third Embodiment]
<Configuration of Recovering Apparatus>

Figure 6:
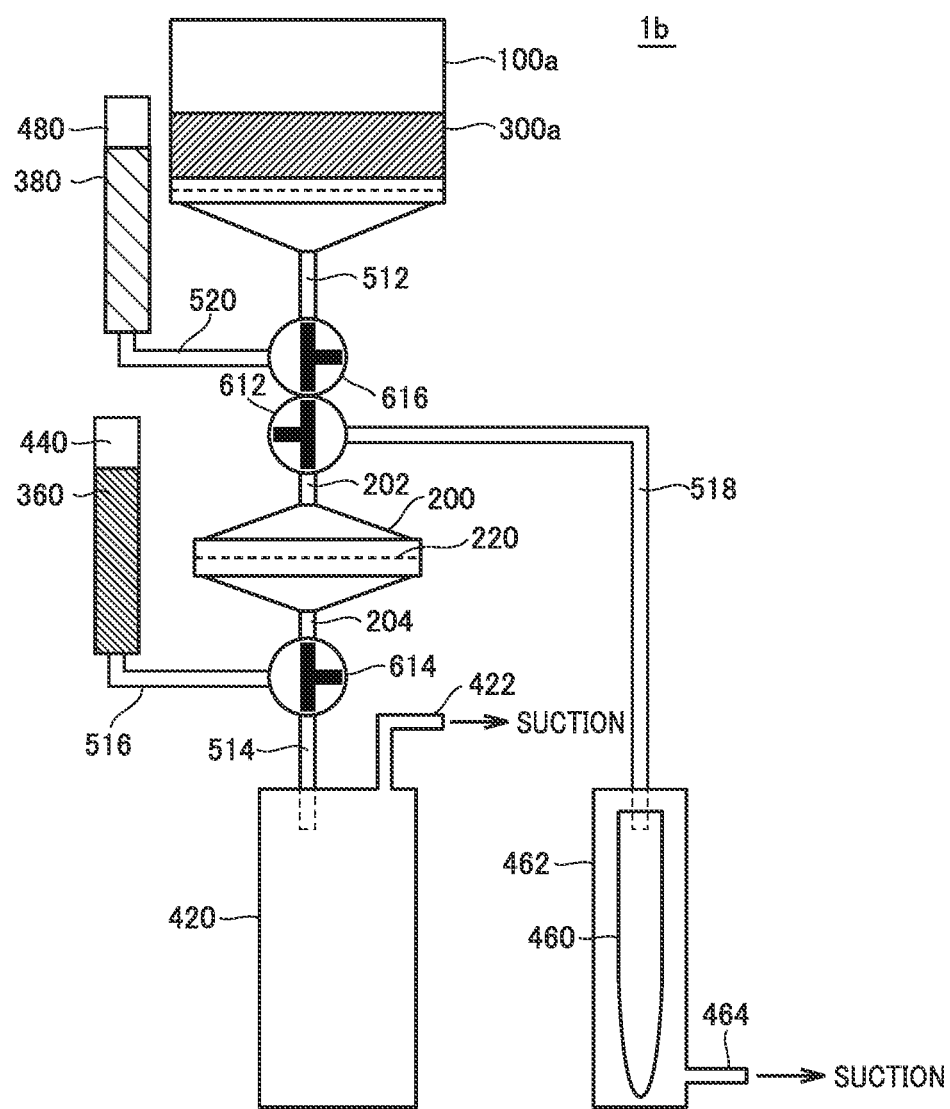
FIG. 6 is a diagram schematically showing an overall configuration of a recovering apparatus according to a third embodiment.

FIG. 6 is a diagram schematically showing an overall configuration of a recovering apparatus according to a third embodiment. A recovering apparatus 1b according to the third embodiment is different from recovering apparatus 1a according to the second embodiment in including a cleaning container 480 that receives a cleaning solution 380, a cleaning path 520, and a third switch 616. Differences of recovering apparatus 1b from recovering apparatus 1a will mainly be described below.

Third switch 616 instead of sample path 512 is connected to first switch 612. In addition to first switch 612, sample path 512 and cleaning path 520 extending to cleaning container 480 are connected to third switch 616.

By operating first switch 612, a flow path in fluid connection to inlet port 202 of filtration apparatus 200 can be switched to a flow path in fluid connection with third switch 616 being interposed or to recovering path 518. By operating third switch 616, a flow path in fluid connection to first switch 612 can be switched to sample path 512 or cleaning path 520.

For example, a three-way turncock is adopted as third switch 616. Third switch 616 may be a switch requiring a manual operation or an electrical switch. First switch 612 and third switch 616 may be implemented by a single switch.

By operating first switch 612 and third switch 616, a flow path in fluid connection to inlet port 202 of filtration apparatus 200 can be switched to sample path 512, recovering path 518, or cleaning path 520.

In the third embodiment, a flow path formed by connection of sample path 512 and inlet port 202 to each other with third switch 616 and first switch 612 being interposed for a flow of fluid and connection of outlet port 204 and waste fluid path 514 to each other with second switch 614 being interposed for a flow of fluid corresponds to the "first flow path."

A flow path formed by connection of recovering path 518 and inlet port 202 to each other with first switch 612 being interposed for a flow of fluid and connection of outlet port 204 and culture medium path 516 to each other with second switch 614 being interposed for a flow of fluid corresponds to the "second flow path."

A flow path formed by connection of cleaning path 520 and inlet port 202 to each other with third switch 616 and first switch 612 being interposed for a flow of fluid and connection of outlet port 204 and waste fluid path 514 to each other with second switch 614 being interposed for a flow of fluid corresponds to the "third flow path."

A flow path formed in recovering apparatus 1b by operating first switch 612, second switch 614, and third switch 616 can be switched to the first flow path, the second flow path, or the third flow path.

<Recovering Method>

Figure 7:
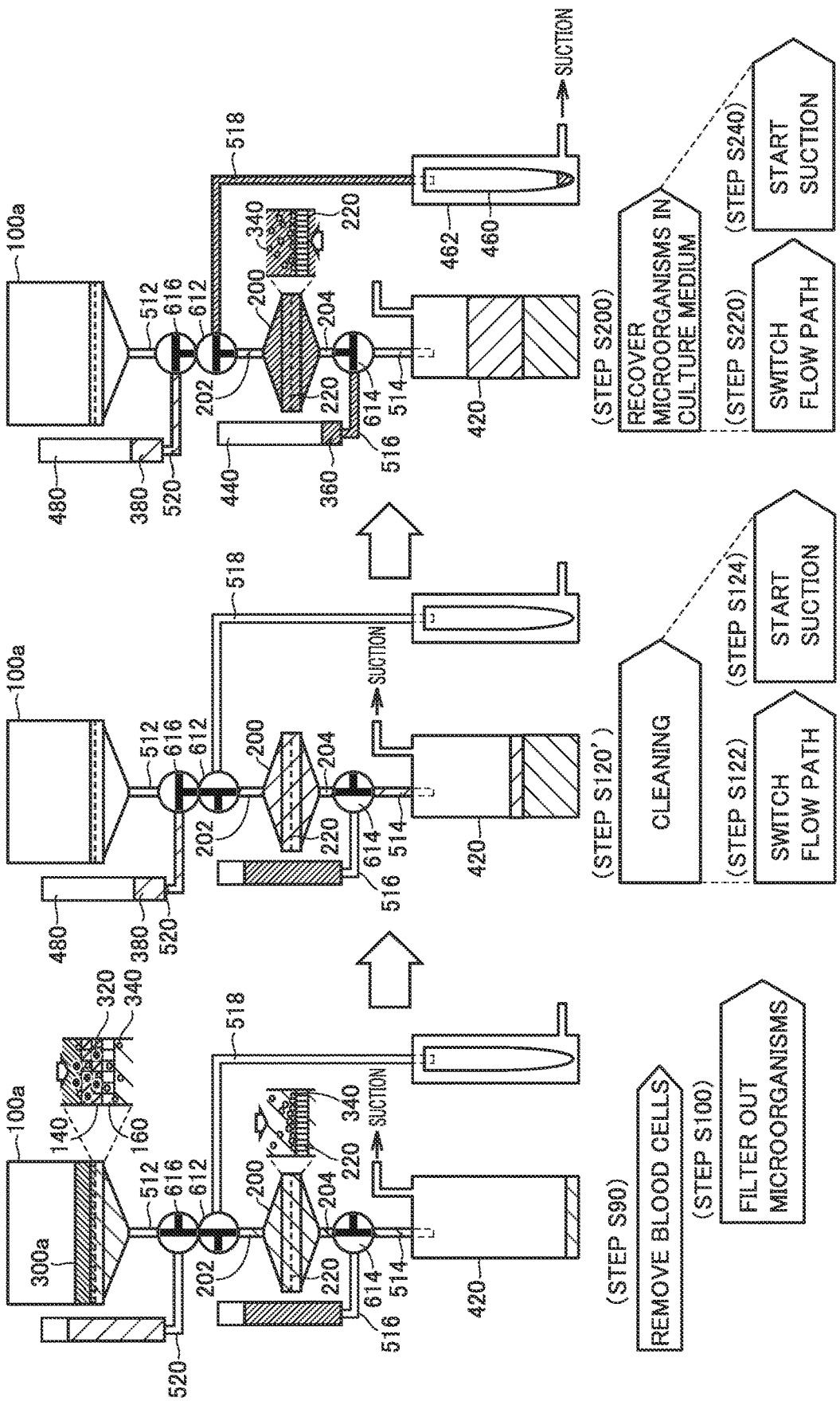
FIG. 7 is a diagram showing overview of a flow of a microorganism recovering method using the recovering apparatus according to the third embodiment.

A microorganism recovering method using recovering apparatus 1b according to the third embodiment will be described. FIG. 7 is a diagram showing overview of a flow of a microorganism recovering method using the recovering apparatus according to the third embodiment.

The microorganism recovering method using recovering apparatus 1b according to the third embodiment is different from the microorganism recovering method (see FIG. 5) using recovering apparatus 1a according to the second embodiment in including a cleaning step S120' instead of cleaning step S120.

After full amount filtration of liquid sample 300a and step S90 of removing blood cells and step S100 of filtering out microorganisms, cleaning step S120' is performed. Cleaning step S120' includes a step S122 of switching a flow path and a step S124 of starting suction.

In step S122, third switch 616 is operated to switch a flow path to be connected to inlet port 202 of filtration apparatus 200 with first switch 612 being interposed from sample path 512 to cleaning path 520. That is, in step S122, a flow path connected to the first end on the side of inlet port 202 switches to cleaning path 520. Cleaning solution 380 in cleaning container 480 can thus flow to filtration apparatus 200.

Step S124 is performed after step S122, and a pressure in waste fluid container 420 is reduced by driving the vacuum pump. Cleaning solution 380 thus flows from cleaning path 520 into waste fluid path 514 and catch filter 220 is cleaned with cleaning solution 380. That is, in step S120', cleaning solution 380 is fed from the first end on the side of inlet port 202 to the second end on the side of outlet port 204.

By cleaning catch filter 220, a substance smaller than microorganisms 340 attached to catch filter 220 or a substance that clogs a gap between microorganisms 340 deposited on catch filter 220 can be removed. Consequently, introduction of such a substance at the time of feed of culture medium 360 can be prevented and microorganisms 340 can be recovered with high purity.

Since the cleaning step is performed simply by switching a flow path to be connected to filtration apparatus 200 by operating third switch 616 in recovering apparatus 1b, an operation is easy. Sample container 100 according to the first embodiment may be employed in the third embodiment, instead of blood cell removal apparatus 100a.

[Modification]

Though an example in which switching among the "first flow path," the "second flow path," and the "third flow path" is made by providing a switch such as a three-way turncock between filtration apparatus 200 and each flow path is shown in the first to third embodiments, a method of switching a flow path, that is, a method of controlling how fluid flows, is not limited thereto. For example, how fluid flows may be controlled by providing a check valve in at least one of flow paths. Specifically, in recovering apparatuses 1 and 1a, a check valve may be provided in sample path 512 to prevent a flow from filtration apparatus 200 into a sample container that receives liquid sample 300 or 300a to thereby control culture medium 360 to flow from filtration apparatus 200 toward recovering path 518. In recovering apparatus 1b, a check valve may be provided in sample path 512 and cleaning path 520 to prevent a flow from filtration apparatus 200 toward blood cell removal apparatus 100a and cleaning path 520 to thereby control culture medium 360 to flow from filtration apparatus 200 toward recovering path 518. In recovering apparatus 1, 1a, or 1b, a check valve may be provided in culture medium path 516 to prevent filtrate from flowing from filtration apparatus 200 toward culture medium path 516 to thereby control filtrate to flow from filtration apparatus 200 toward waste fluid path 514.

The method of recovering microorganisms described with reference to the first to third embodiments is not limited to the method using an apparatus shown in recovering apparatus 1, 1a, or 1b. So long as culture medium 360 can flow in a direction reverse to a direction of flow of liquid sample 300 or 300a in feeding culture medium 360 to filtration apparatus 200, the method is not limited to the method using an apparatus shown in recovering apparatus 1, 1a, or 1b.

The configuration of each recovering apparatus 1, 1a, or 1b shown in the first to third embodiments is by way of example, and arrangement of each component (a container and an apparatus) is not limited to arrangement in the configuration shown in each of recovering apparatuses 1, 1a, and 1b.

In the first to third embodiments, an example in which a pressure in waste fluid container 420 is reduced, microorganisms 340 are filtered out through filtration apparatus 200, liquid sample 300a is filtered through first filter 140 and second filter 160, or cleaning solution 380 is fed into filtration apparatus 200 is shown. A method of feeding a liquid into recovering apparatus 1, 1a, or 1b is not limited to the method of reducing a pressure on an outlet side (a secondary side). For example, the method may be performed by increasing a pressure on an inlet side (a primary side) or by reducing a pressure on the outlet side (the secondary side) and increasing a pressure on the inlet side (the primary side).

Similarly, the method of feeding culture medium 360 into filtration apparatus 200 is not limited to the method of reducing a pressure in suction box 462. A method of increasing a pressure on a side of culture medium container 440, or a method of reducing a pressure on a side of recovering container 460 and increasing a pressure on the side of culture medium container 440 may be applicable.

An example in which recovering container 460 is arranged in suction box 462 is shown in the first to third embodiments. Recovering container 460 may function as suction box 462, and the function of suction box 462 and the function of recovering container 460 may be performed by a single apparatus.

In the second and third embodiments, first filter 140 is stacked on second filter 160, however, the arrangement is not limited thereto. For example, first filter 140 and second filter 160 may be arranged in close contact with each other in blood cell removal apparatus 100a. Alternatively, first filter 140 and second filter 160 may be integrally formed. As long as microorganisms 340 may pass through second filter 160 before clogging occurs due to the accumulation of blood cells 320 on second filter 160, first filter 140 may not be stacked on second filter 160 or a gap may be provided between first filter 140 and second filter 160.

Though culture medium 360 (a liquid culture medium) is adopted as a liquid (recovering fluid) for recovering microorganisms 340 in the first to third embodiments, a liquid for recovering microorganisms 340 is not limited to culture medium 360. The recovering fluid can be selected in accordance with an operation after recovering, and for example, a buffer adjusted to pH at which microorganisms 340 to be recovered are not killed may be applicable.

[Fourth Embodiment]

<Configuration of Recovering Apparatus>

Figure 8:
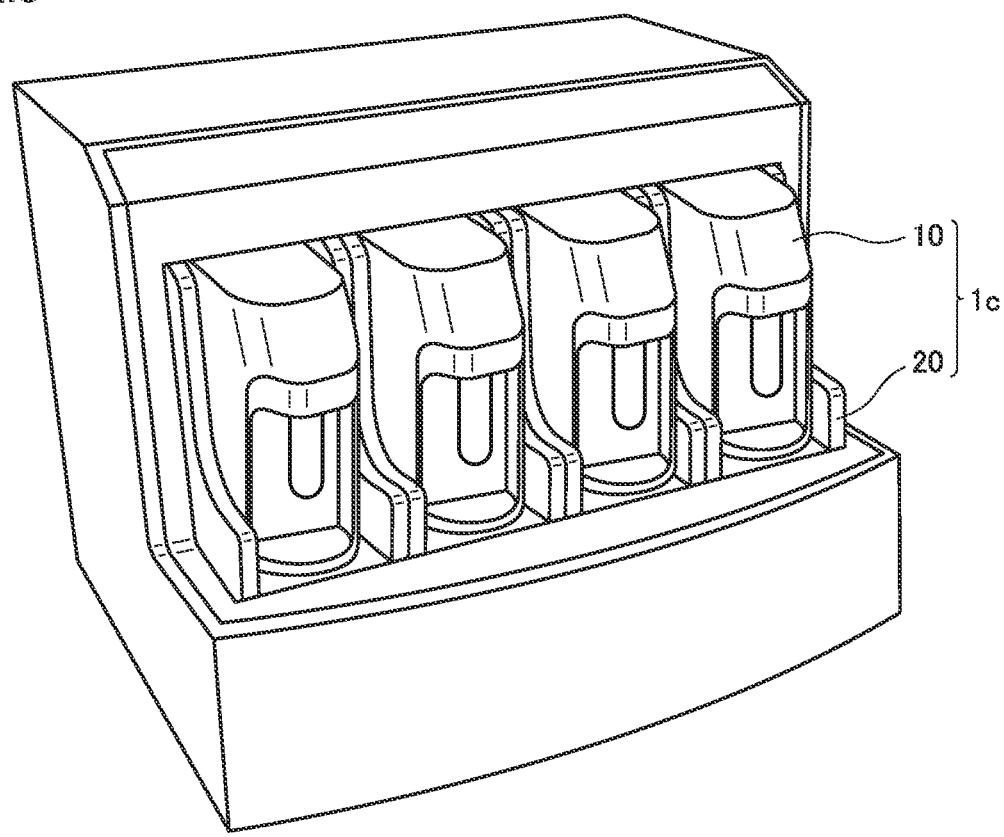
FIG. 8 is a schematic perspective view of a recovering apparatus according to a fourth embodiment.
Figure 9:
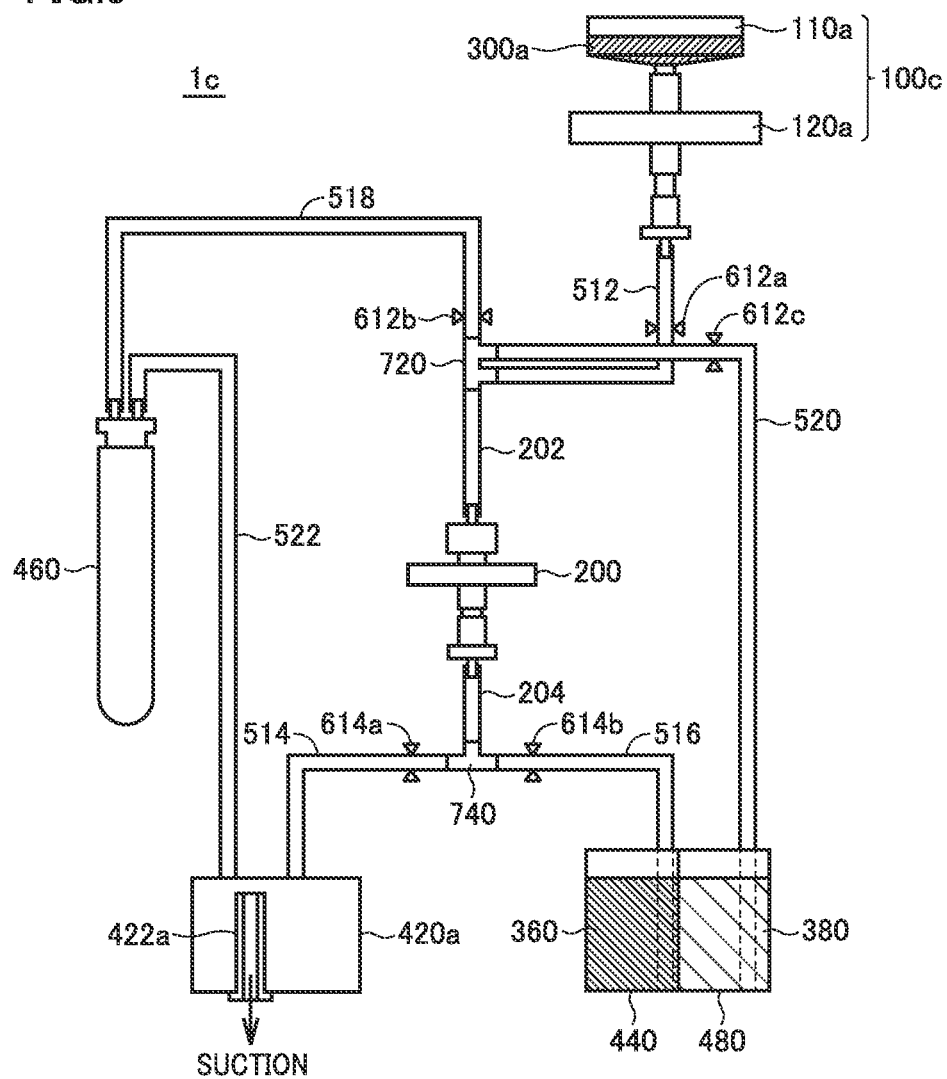
FIG. 9 is a diagram schematically showing an overall configuration of the recovering apparatus according to the fourth embodiment.

FIG. 8 is a schematic perspective view of a recovering apparatus according to a fourth embodiment. FIG. 9 is a diagram schematically showing an overall configuration of the recovering apparatus according to the fourth embodiment. A recovering apparatus 1c according to the fourth embodiment is different from recovering apparatus 1b according to the third embodiment in further including a housing 10, an enclosure 20, a suction path 522, a first connector 720, and a second connector 740. Recovering apparatus 1c according to the fourth embodiment is further different from recovering apparatus 1b according to the third embodiment in including a blood cell removal apparatus 100c instead of blood cell removal apparatus 100a, including first switches 612a, 612b, and 612c and second switches 614a and 614b instead of first switch 612, second switch 614, and third switch 616, and including a waste fluid container 420a instead of waste fluid container 420 and suction box 462.

Referring to FIG. 8, recovering apparatus 1c includes housing 10 and enclosure 20. The example shown in FIG. 8 discloses an apparatus in which four recovering apparatuses 1c are integrated and does not show some of reference numerals.

Referring to FIG. 9, recovering apparatus 1c includes blood cell removal apparatus 100c, filtration apparatus 200, waste fluid container 420a, culture medium container 440, recovering container 460, cleaning container 480, first switches 612a, 612b, and 612c, and second switches 614a and 614b.

Though description will be given later with reference to FIGS. 10 and 11, blood cell removal apparatus 100c, filtration apparatus 200, waste fluid container 420a, culture medium container 440, cleaning container 480, and a flow path that connects containers are accommodated in housing 10. Recovering container 460 is removably supported by housing 10. In housing 10, a component contaminated by liquid sample 300a or the like, repeated use of which is difficult, is arranged.

Though description will be given later with reference to FIG. 13, first switches 612a, 612b, and 612c, second switches 614a and 614b, a vacuum pump, and a suction tube 424a connected to the vacuum pump are arranged in enclosure 20. In enclosure 20, a component controlled by a controller including a central processing unit (CPU) in automating recovering of microorganisms is arranged.

Blood cell removal apparatus 100c according to the fourth embodiment shown in FIG. 9 includes a container 110a that receives liquid sample 300a and a filtration apparatus 120a where first filter 140 and second filter 160 are arranged. Container 110a and filtration apparatus 120a are coupled to each other.

Sample path 512 that extends to blood cell removal apparatus 100c, recovering path 518 that extends to recovering container 460, and cleaning path 520 that extends to cleaning container 480 are connected to inlet port 202 that extends from filtration apparatus 200, with first connector 720 being interposed.

A point of merge between sample path 512 and inlet port 202 (a point of connection to first connector 720) is preferably located closer to filtration apparatus 200 than a point of merge between cleaning path 520 and inlet port 202 (a point of connection to first connector 720). According to the configuration as such, liquid sample 300a that remains in first connector 720 (liquid sample 300a out of which blood cells have been removed) can sufficiently be washed away when cleaning solution 380 is fed, and contamination of culture medium 360 can be prevented.

A point of merge between recovering path 518 and inlet port 202 (a point of connection to first connector 720) may be located closer to filtration apparatus 200 than the point of merge between cleaning path 520 and inlet port 202 (the point of connection to first connector 720). According to the configuration as such, culture medium 360 passes through at least the flow path through which cleaning solution 380 has passed, of the flow path through which liquid sample 300a (liquid sample 300a out of which blood cells have been removed) has passed, and hence contamination of culture medium 360 can be prevented.

Waste fluid path 514 that extends to waste fluid container 420a and culture medium path 516 that extends to culture medium container 440 are connected to outlet port 204 that extends from filtration apparatus 200, with second connector 740 being interposed.

First connector 720 and second connector 740 do not perform a function to switch a flow path but merely perform a function to branch a flow path. Inlet port 202 and outlet port 204 are exemplary embodiments of the first opening and the second opening in the invention of the present application. The flow path that extends from each of the first opening and the second opening should only be branched, and a branching method is not limited to the method of providing first connector 720 and second connector 740.

First switches 612a, 612b, and 612c and second switches 614a and 614b according to the fourth embodiment all cut off a flow path by pinching and compressing a tube that forms the flow path, and they are each implemented by a pinch valve. First switches 612a, 612b, and 612c and second switches 614a and 614b cut off or open a flow path by adjusting an external pressure to be applied to the flow path.

First switch 612a is arranged in enclosure 20 to pinch sample path 512 when housing 10 is attached to enclosure 20. First switch 612a cuts off sample path 512 by compressing sample path 512 to cut off fluid connection between blood cell removal apparatus 100c and inlet port 202. On the other hand, first switch 612a opens sample path 512 by canceling compression of sample path 512 to bring blood cell removal apparatus 100c and inlet port 202 in fluid connection to each other.

First switch 612b is arranged in enclosure 20 to pinch recovering path 518 when housing 10 is attached to enclosure 20. First switch 612b cuts off recovering path 518 by compressing recovering path 518 to cut off fluid connection between recovering container 460 and inlet port 202. On the other hand, first switch 612b opens recovering path 518 by canceling compression of recovering path 518 to bring recovering container 460 and inlet port 202 in fluid connection to each other.

First switch 612c is arranged in enclosure 20 to pinch cleaning path 520 when housing 10 is attached to enclosure 20. First switch 612c cuts off cleaning path 520 by compressing cleaning path 520 to cut off fluid connection between cleaning container 480 and inlet port 202. On the other hand, first switch 612c opens cleaning path 520 by canceling compression of cleaning path 520 to bring cleaning container 480 and inlet port 202 in fluid connection to each other.

Second switch 614a is arranged in enclosure 20 to pinch waste fluid path 514 when housing 10 is attached to enclosure 20. Second switch 614a cuts off waste fluid path 514 by compressing waste fluid path 514 to cut off fluid connection between waste fluid container 420a and outlet port 204. On the other hand, second switch 614a opens waste fluid path 514 by canceling compression of waste fluid path 514 to bring waste fluid container 420a and outlet port 204 in fluid connection to each other.

Second switch 614b is arranged in enclosure 20 to pinch culture medium path 516 when housing 10 is attached to enclosure 20. Second switch 614b cuts off culture medium path 516 by compressing culture medium path 516 to cut off fluid connection between culture medium container 440 and outlet port 204. On the other hand, second switch 614b brings culture medium container 440 and outlet port 204 in fluid connection to each other by canceling compression of culture medium path 516.

Opening the flow path may be referred to as opening the switch and cutting off the flow path may be referred to as closing the switch below.

By opening first switch 612a and second switch 614a and closing first switches 612b and 612c and second switch 614b, sample path 512 and inlet port 202 are in fluid connection to each other and outlet port 204 and waste fluid path 514 are in fluid connection to each other. The flow path formed by such connection corresponds to the "first flow path."

By opening first switch 612b and second switch 614b and closing first switches 612a and 612c and second switch 614a, recovering path 518 and inlet port 202 are in fluid connection to each other and outlet port 204 and culture medium path 516 are in fluid connection to each other. The flow path formed by such connection corresponds to the "second flow path."

By opening first switch 612c and second switch 614a and closing first switches 612a and 612b and second switch 614bcleaning path 520 and inlet port 202 are in fluid connection to each other and outlet port 204 and waste fluid path 514 are in fluid connection to each other. The flow path formed by such connection corresponds to the "third flow path."

As set forth above, recovering apparatus 1c according to the fourth embodiment switches among the first flow path, the second flow path, and the third flow path by compressing a tube or canceling compression of the tube pinched by each of first switches 612a, 612b, and 612c and second switches 614a and 614b.

In the fourth embodiment, waste fluid container 420a functions as the waste fluid container that receives waste fluid and the suction box for reducing a pressure in recovering container 460. More specifically, waste fluid path 514 that extends from second connector 740 to which outlet port 204 is connected and suction path 522 that extends from recovering container 460 are connected to waste fluid container 420a. By reducing a pressure in waste fluid container 420a while the "first flow path" or the "third flow path" is formed, filtrate (waste fluid) discharged from outlet port 204 is accommodated in waste fluid container 420a. On the other hand, by reducing a pressure in waste fluid container 420a while the "second flow path" is formed, culture medium 360 in culture medium container 440 is accommodated in recovering container 460 sequentially through culture medium path 516, second connector 740, outlet port 204, filtration apparatus 200, inlet port 202, first connector 720, and recovering path 518.

<Configuration of Housing>

Figure 10:
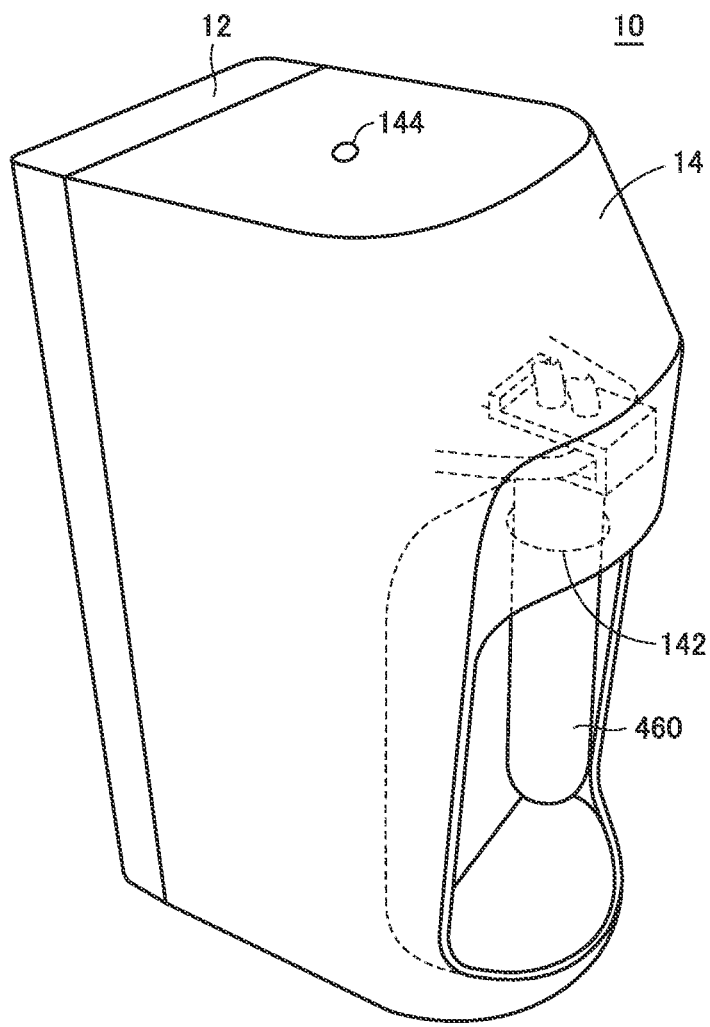
FIG. 10 is a schematic perspective view of a housing shown in FIG. 8.

FIG. 10 is a schematic perspective view of the housing shown in FIG. 8. FIG. 11 is a schematic perspective view showing a state that a cover has been removed from the housing shown in FIG. 10. FIG. 12 is a schematic rear view of the housing shown in FIG. 10. FIG. 10 shows a part hidden by a cover 14 with a dashed line. FIG. 11 does not show a flow path that connects each container and the filtration apparatus to each other for simplified illustration.

Referring to FIG. 10, housing 10 includes a main body 12 and cover 14 attached to main body 12. In cover 14, an opening 142 and an introduction port 144 for introduction of liquid sample 300a are provided.

In housing 10, a connection portion 466 (see FIG. 11) is arranged at a position opposed to opening 142. Recovering path 518 that extends from first connector 720 and suction path 522 that extends from waste fluid container 420a are fixed to connection portion 466.

Recovering container 460 has one open end and is attachable to and removable from connection portion 466. Recovering container 460 has such a size as allowing insertion thereof into housing 10 through opening 142, and it can be attached to or removed from connection portion 466 arranged in housing 10 through opening 142. Recovering container 460 is thus removably supported by housing 10.

In housing 10, container 110a of blood cell removal apparatus 100c is arranged at a position opposed to introduction port 144 provided in cover 14. Therefore, when liquid sample 300a is introduced through introduction port 144, container 110a receives introduced liquid sample 300a.

Figure 11:
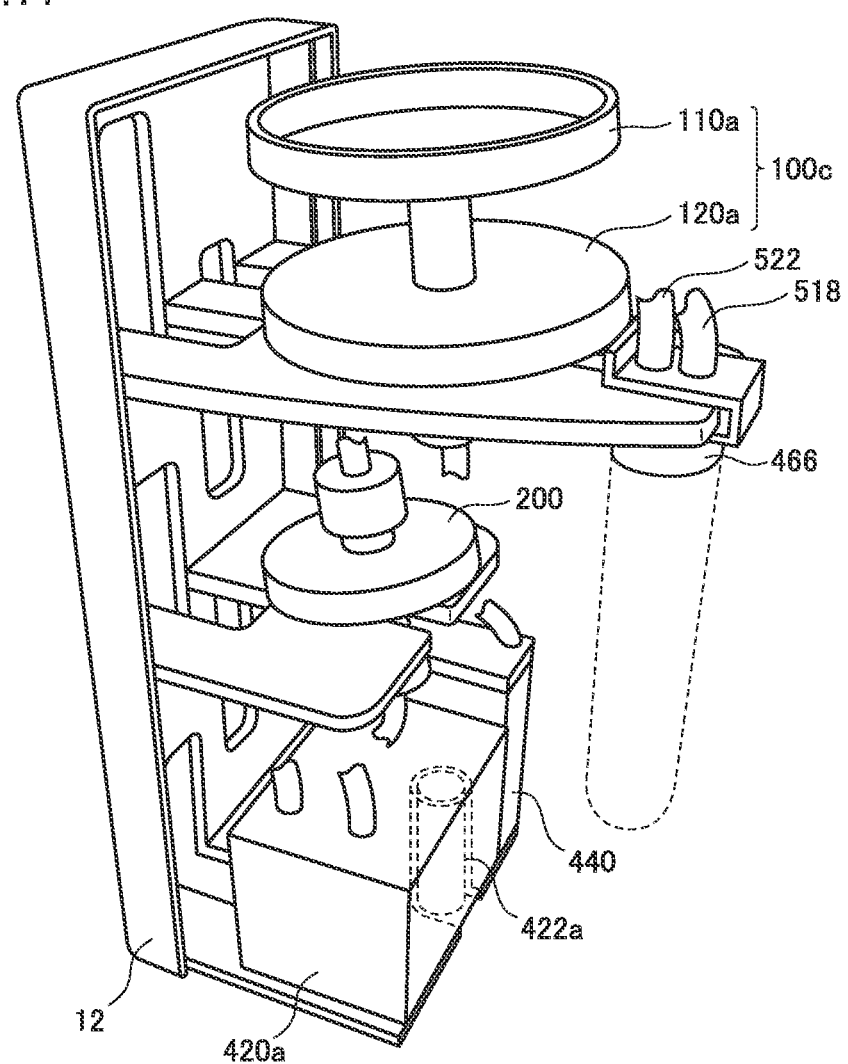
FIG. 11 is a schematic perspective view showing a state that a cover has been removed from the housing shown in FIG. 10.
Figure 12:
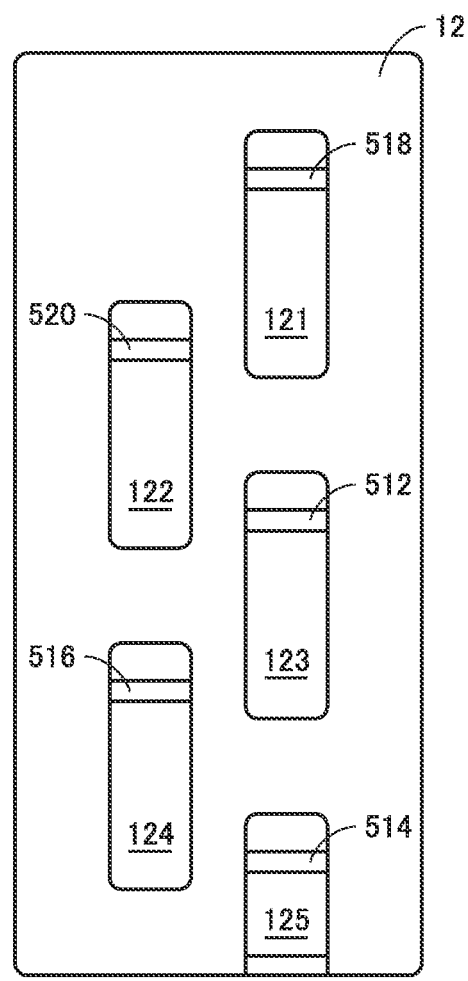
FIG. 12 is a schematic rear view of the housing shown in FIG. 10.

As shown in FIGS. 10 and 11, at least a part of recovering container 460 is exposed in housing 10. Blood cell removal apparatus 100c, filtration apparatus 200, waste fluid container 420a, culture medium container 440, cleaning container 480 (not shown), and a flow path that connects these components are all accommodated in housing 10. Therefore, a portion touched by a human's hand can be limited to minimum necessary, contamination is less likely, and infection from liquid sample 300a can be prevented.

Referring to FIG. 11, blood cell removal apparatus 100c, filtration apparatus 200, waste fluid container 420a, culture medium container 440, cleaning container 480, and connection portion 466 are arranged in main body 12.

Referring to FIG. 12, five openings 121 to 125 are provided in a rear surface of main body 12. Recovering path 518 that extends to recovering container 460 is arranged in main body 12 to extend across opening 121. Cleaning path 520 that extends to cleaning container 480 is arranged in main body 12 to extend across opening 122. Sample path 512 that extends to blood cell removal apparatus 100c is arranged in main body 12 to extend across opening 123. Culture medium path 516 that extends to culture medium container 440 is arranged in main body 12 to extend across opening 124. Waste fluid path 514 that extends to waste fluid container 420a is arranged in main body 12 to extend across opening 125.

At least portions of recovering path 518, cleaning path 520, sample path 512, culture medium path 516, and waste fluid path 514 that extend across respective openings 121 to 125 are formed from plastic tubes.

<Configuration of Enclosure>

Figure 13:
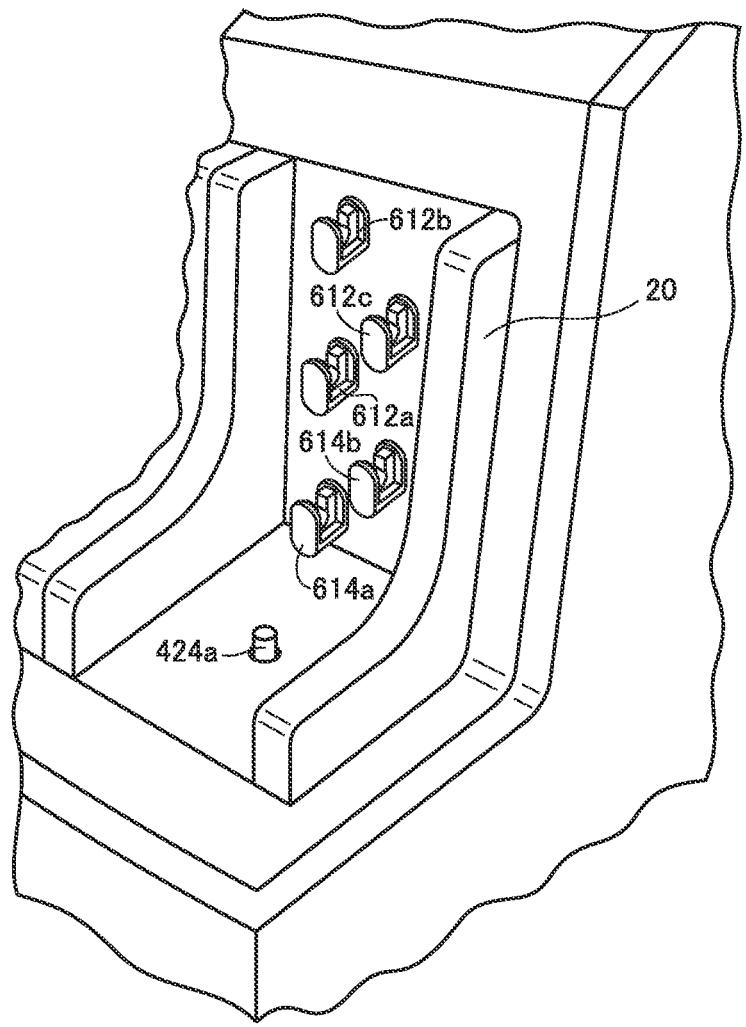
FIG. 13 is a schematic perspective view showing an enclosure shown in FIG. 8.

FIG. 13 is a schematic perspective view showing the enclosure shown in FIG. 8. Referring to FIG. 13, in enclosure 20, first switches 612a, 612b, and 612c, second switches 614a and 614b, and suction tube 424a are arranged. Though not shown, a controller that controls each of first switches 612a, 612b, and 612c, second switches 614a and 614b, and a suction pump (vacuum pump) connected to suction tube 424a is provided in enclosure 20. A single controller may be provided for four recovering apparatuses 1c or controllers may be provided for four recovering apparatuses 1c, respectively.

First switches 612a, 612b, and 612c and second switches 614a and 614b are arranged in a surface opposed to the rear surface of main body 12 where openings 121 to 125 are provided when housing 10 is attached to enclosure 20.

More specifically, first switch 612b is arranged at a position opposed to opening 121 when housing 10 is attached to enclosure 20. First switch 612c is arranged at a position opposed to opening 122 when housing 10 is attached to enclosure 20. First switch 612a is arranged at a position opposed to opening 123 when housing 10 is attached to enclosure 20. Second switch 614b is arranged at a position opposed to opening 124 when housing 10 is attached to enclosure 20. Second switch 614a is arranged at a position opposed to opening 125 when housing 10 is attached to enclosure 20.

According to such arrangement, when housing 10 is attached to enclosure 20, first switch 612b pinches recovering path 518 that extends across opening 121. Similarly, first switch 612c pinches cleaning path 520 that extends across opening 122. First switch 612a pinches sample path 512 that extends across opening 123. Second switch 614b pinches culture medium path 516 that extends across opening 124. Second switch 614a pinches waste fluid path 514 that extends across opening 125.

As enclosure 20 and housing 10 are configured as above, a desired switch is attached to each flow path as shown in FIG. 9 when housing 10 is attached to enclosure 20.

Suction tube 424a is provided at a position opposed to a surface (a bottom surface) where a suction portion 422a of waste fluid container 420a accommodated in housing 10 is located when housing 10 is attached to enclosure 20. Suction tube 424a can thus be attached to suction portion 422a when housing 10 is attached to enclosure 20.

A switch (first switches 612a, 612b, and 612c and second switches 614a and 614b) for switching among flow paths should be controlled by the controller in automating recovering of microorganisms. Flow paths, switching among which is made by the switch, are contaminated by liquid sample 300a or the like, repeated use thereof is difficult, and the flow path is preferably disposed of each time it is used.

Therefore, when a switch and a flow path are integrally formed, the switch should also be disposed of together with the flow path, which gives rise to a problem of necessity for connection between the switch and the controller each time in a plurality of times of use or increase in cost.

Recovering apparatus 1c according to the fourth embodiment is configured such that the switch (first switches 612a, 612b, and 612c and second switches 614a and 614b) for switching among the flow paths externally pinches the flow path like a pinch valve. Therefore, the switch and the flow path can be separate from each other. In automating recovering of microorganisms, a component that should be controlled by the controller and a component contaminated by liquid sample 300a or the like can thus be separate from each other and usability in a plurality of times of use is improved.

In recovering apparatus 1c according to the fourth embodiment, each switch for switching among the flow paths is arranged in enclosure 20, as being attached to a corresponding flow path when housing 10 is attached to enclosure 20. Therefore, a user can use recovering apparatus 1c simply by attaching or removing non-reusable housing 10 to enclosure 20.

Though recovering apparatus 1c according to the fourth embodiment is premised on implementation of a microorganism recovering method including a cleaning step, it does not have to include cleaning container 480 and cleaning path 520, for example, when the cleaning step is not required. The cleaning step may be performed by introducing cleaning solution 380 through introduction port 144 while the first flow path is formed.

Recovering apparatus 1c according to the fourth embodiment includes blood cell removal apparatus 100c including first filter 140 and second filter 160 and is premised on treatment of liquid sample 300a containing blood cells. As in the first embodiment, recovering apparatus 1c according to the fourth embodiment also functions as an apparatus that treats liquid sample 300 that does not contain blood cells. In this case, recovering apparatus 1c may include sample container 100 instead of blood cell removal apparatus 100c.

In recovering apparatus 1c according to the fourth embodiment, a single switch is connected to each flow path that is to be cut off/opened. The number of switches, however, does not necessarily have to be equal to the number of flow paths to be cut off/opened, and for example, the number of necessary switches may be reduced by moving a position of the switch. At least one of switches may be a check valve so that the number of switches that cut off or open a flow path by compression is reduced.

In recovering apparatus 1c according to the fourth embodiment, blood cell removal apparatus 100c, filtration apparatus 200, waste fluid container 420a, culture medium container 440, cleaning container 480, and a flow path that connects these components are all accommodated in housing 10. At least a portion (a tube) to which each switch is attached, of the flow path that connects the components should only be arranged in housing 10. Waste fluid container 420a, culture medium container 440, and cleaning container 480 do not have to be accommodated in housing 10. For example, waste fluid container 420a, culture medium container 440, and cleaning container 480 may be separate from housing 10 and enclosure 20. Waste fluid container 420a, culture medium container 440, and cleaning container 480 may be provided in enclosure 20.

<Exemplary Recovering Process>

Figure 14:
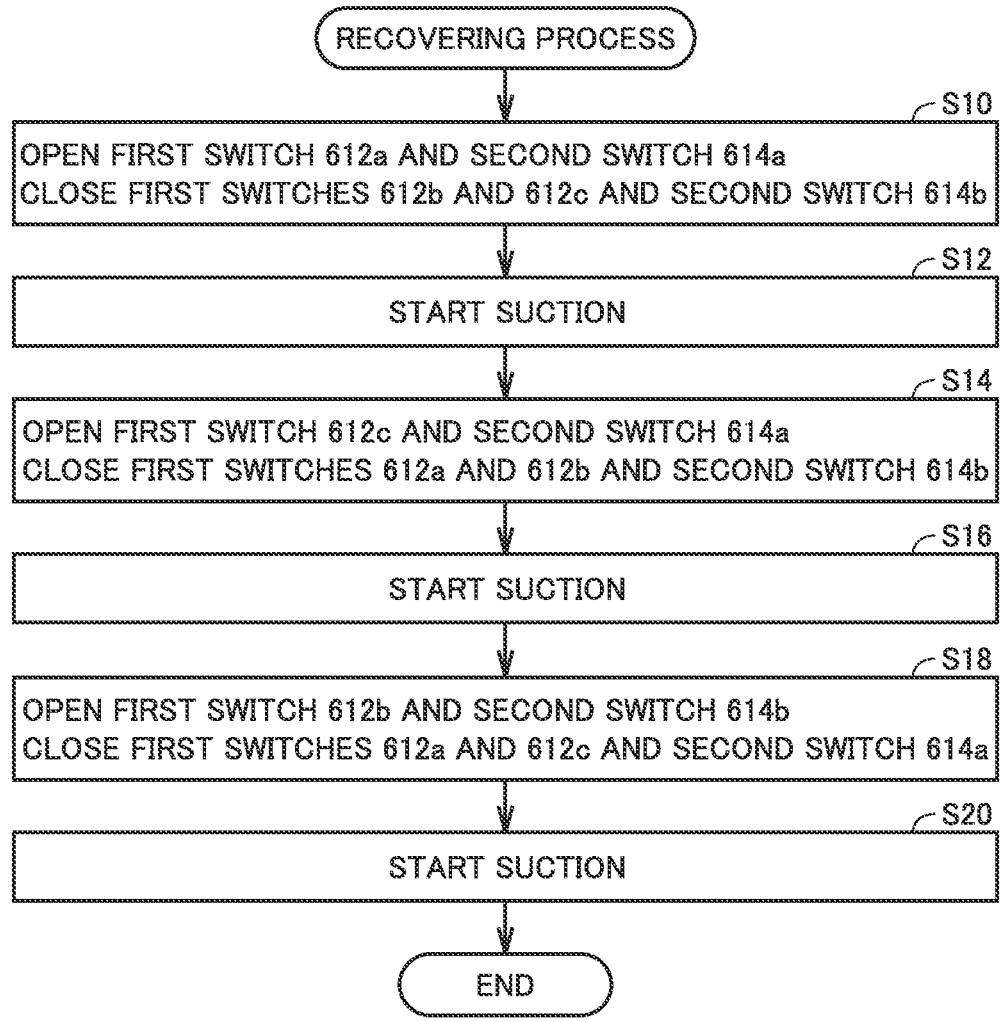
FIG. 14 is a flowchart showing a recovering process performed by a controller.

FIG. 14 is a flowchart showing a recovering process performed by the controller. Though not shown, the controller includes a CPU, a storage that stores a program and data, and a communication interface (I/F) as main constituent elements. The storage includes a read only memory (ROM), a random access memory (RAM), and a hard disk drive (HDD). The ROM stores a program to be executed by the CPU. The RAM temporarily stores data generated by execution of a program by the CPU and data input through the communication FF. The RAM can function as a temporary data memory that is used as a work area. The HDD is a non-volatile storage device. Instead of the HDD, a semiconductor storage device such as a flash memory may be adopted.

A program stored in the ROM may be stored in a storage medium and distributed as a program product. Alternatively, a program may be provided by an information provider, as a program product that can be downloaded through what is called the Internet.

A storage medium is not limited to a digital versatile disk read only memory (DVD-ROM), a compact disc read-only memory (CD-ROM), a flexible disk (FD), and a hard disk, and may be a medium that carries a program in a fixed manner such as a magnetic tape, a cassette tape, an optical disc (a magneto-optical (MO) disc/a mini disc (MD)/a digital versatile disc (DVD)), an optical card, and a semiconductor memory such as a mask ROM, an electronically programmable read-only memory (EPROM), an electronically erasable programmable read-only memory (EEPROM), and a flash ROM. A recording medium is a non-transitory medium from which a computer can read a program.

The recovering process shown in FIG. 14 is performed by execution of a program by the CPU of the controller. The recovering process is performed based on attachment of housing 10 to enclosure 20 and an operation onto a not-shown start switch. Some or all of functions provided by the recovering process may be implemented by a dedicated hardware circuit (for example, an application specific integrated circuit (ASIC) or a field-programmable gate array (FPGA)).

In S10, the controller controls first switch 612a and second switch 614a to open and controls first switches 612b and 612c and second switch 614b to close. The first flow path is thus formed.

In S12, the controller starts suction. Specifically, the vacuum pump connected to suction tube 424a is driven. Step (S90) of removing blood cells and step (S100) of filtering out microorganisms shown in FIG. 7 are performed.

In S14, the controller controls first switch 612c and second switch 614a to open and controls first switches 612a and 612b and second switch 614b to close. More specifically, the controller controls first switch 612c to open and controls first switch 612a to close. Switching from the first flow path to the third flow path is thus made and step (S122) of switching the flow path shown in FIG. 7 is performed.

In S16, the controller starts suction. Specifically, the vacuum pump connected to suction tube 424a is driven. By performing S14 and S16, the cleaning step (S120') shown in FIG. 7 is performed.

In S18, the controller controls first switch 612b and second switch 614b to open and controls first switches 612a and 612c and second switch 614a to close. More specifically, the controller controls first switch 612b and second switch 614b to open and controls first switch 612c and second switch 614a to close. Switching from the third flow path to the second flow path is thus made and step (S220) of switching the flow path shown in FIG. 7 is performed.

In S20, the controller starts suction and thereafter quits the recovering process. Specifically, the vacuum pump connected to suction tube 424a is driven. By performing S18 and S20, step (S200) of recovering microorganisms in the culture medium shown in FIG. 7 is performed.

Though processing for stopping suction is not included in the flowchart shown in FIG. 14, the controller performs processing for stopping suction after S12, S16, and S20.

[Aspects]

A person skilled in the art would understand that the plurality of exemplary embodiments and the modifications thereof described above represent specific examples of aspects below.

(Clause 1)

A microorganism recovering method according to one aspect includes steps of filtering out microorganisms from a liquid sample through a filtration apparatus, the filtration apparatus including a first end and a second end, the filtration apparatus being configured to receive the liquid sample at the first end and being configured to discharge from the second end filtrate generated through the filtering out microorganisms and recovering the microorganisms filtered out by the filtration apparatus together with recovering fluid by feeding the recovering fluid from the second end to the first end.

According to such a configuration, since microorganisms can be separated and recovered from the filtration apparatus with force of flow of the recovering fluid, recovering of microorganisms can be automated.

(Clause 2)

In the microorganism recovering method described in Clause 1, the recovering fluid is a liquid culture medium to be used for culturing the microorganisms.

According to such a configuration, after microorganisms filtered out by the filtration apparatus are recovered together with the recovering fluid, a recovered solution can be used as it is for culturing. Since microorganisms are recovered directly in the liquid culture medium used for culturing, efficiency in recovering microorganisms can be improved.

(Clause 3)

The step of recovering the microorganisms together with the recovering fluid in the microorganism recovering method described in Clause 1 or 2 may include the step of switching a flow path connected to the first end to a recovering path connected to a recovering container into which the recovering fluid containing the microorganisms is recovered.

According to such a configuration, the recovering fluid can flow toward the recovering path by switching the flow path and recovering of microorganisms can be automated by automating switching of the flow path.

(Clause 4)

The microorganism recovering method according to any one of Clauses 1 to 3 may further include the step of feeding a cleaning solution from the first end to the second end. The step of feeding a cleaning solution is performed between the step of filtering out microorganisms and the step of recovering the microorganisms together with the recovering fluid.

According to such a configuration, of substances in the liquid sample attached to the filtration apparatus, a substance smaller than microorganisms or a substance that clogs a gap between microorganisms deposited on the filtration apparatus can be removed by cleaning. Consequently, introduction of such a substance at the time when the recovering fluid is fed can be prevented and microorganisms can be recovered with high purity.

(Clause 5)

The step of feeding a cleaning solution in the microorganism recovering method described in Clause 4 may include the step of switching a flow path to be connected to the first end to a cleaning path connected to a cleaning container that receives the cleaning solution.

According to such a configuration, the cleaning solution can be fed into the filtration apparatus by switching the flow path, and cleaning in the filtration apparatus can be automated by automating switching of the flow path.

(Clause 6)

In the microorganism recovering method described in any one of Clauses 1 to 5, the liquid sample may contain blood cells. In this case, the microorganism recovering method further includes the step of removing the blood cells out of the liquid sample. The step of removing the blood cells is performed before the step of filtering out microorganisms.

According to such a configuration, without special treatment for taken blood, taken blood can be used as a liquid sample.

(Clause 7)

The step of removing the blood cells in the microorganism recovering method described in Clause 6 may include steps of performing, by using a first filter, a first filtration on the liquid sample, the first filter having a filtration resistance against the microorganisms smaller than a filtration resistance against the blood cells, so that the microorganisms generally pass through faster than the blood cells and performing, by using a second filter, a second filtration on a filtrate containing the microorganisms, while the blood cells are retained on the first filter, to selectively permeate the microorganisms by size. The steps of removing the blood cells and filtering out microorganisms may be performed by at least one of increase in pressure on a primary side of the first filtration and pressure reduction on the side where the filtrate is discharged.

According to such a configuration, a unit operation of filtration can be performed on a liquid sample containing blood cells without performing any treatment thereon, and filtrate resulting from removal of blood cells from the liquid sample can be obtained by performing one unit operation. By performing at least one of operations to increase a pressure and to reduce a pressure, the step of removing the blood cells and the step of filtering out microorganisms can be performed and an operation can be simplified.

(Clause 8)

The step of recovering the microorganisms together with the recovering fluid in the microorganism recovering method described in any one of Clauses 1 to 7 may include the step of switching a flow path to be connected to the second end to a flow path connected to a recovering fluid container that receives the recovering fluid.

According to such a configuration, the recovering fluid can be fed into the filtration apparatus by switching the flow path, and recovering of microorganisms can be automated by automating switching of the flow path.

(Clause 9)

A microorganism recovering apparatus according to one aspect includes a sample container that receives a liquid sample, a filtration apparatus including a filter having a pore size smaller than a microorganism and a first opening and a second opening formed at positions opposed to each other with the filter being interposed, a waste fluid container that receives a waste fluid, a recovering fluid container that receives a recovering fluid, a recovering container that receives a solution to be recovered, a first flow path through which the sample container is connected to a side of the first opening of the filtration apparatus and the waste fluid container is connected to a side of the second opening of the filtration apparatus, and a second flow path through which the recovering fluid container is connected to the side of the second opening of the filtration apparatus and the recovering container is connected to the side of the first opening of the filtration apparatus.

By using the microorganism recovering apparatus configured as such, microorganisms can be filtered out in the filtration apparatus by feeding the liquid sample from the sample container, and thereafter microorganisms filtered out in the filtration apparatus can be recovered in the recovering fluid by feeding the recovering fluid toward the filtration apparatus. Therefore, by using the microorganism recovering apparatus, microorganisms can be separated and recovered from the filtration apparatus with force of flow of the recovering fluid and microorganisms can be recovered without a manual operation. Therefore, recovering of microorganisms can be automated.

(Clause 10)

In the microorganism recovering apparatus described in Clause 9, the recovering fluid is a liquid culture medium to be used for culturing the microorganisms.

According to such a configuration, after microorganisms filtered out by the filtration apparatus are recovered together with the recovering fluid, a recovered solution can be used as it is for culturing. Since microorganisms are recovered directly in the liquid culture medium used for culturing, efficiency in recovering microorganisms can be improved.

(Clause 11)

The microorganism recovering apparatus described in Clause 9 or 10 may further include a first switch that switches connection to the first opening to the sample container or the recovering container and a second switch that switches connection to the second opening to the waste fluid container or the recovering fluid container.

By using the microorganism recovering apparatus configured as such, switching from the first flow path to the second flow path can be made simply by operating the first switch and the second switch. By automating the operation onto the first switch and the second switch, recovering of microorganisms can be automated.

(Clause 12)

The microorganism recovering apparatus described in Clause 9 or 10 may further include a cleaning container that receives a cleaning solution and a third flow path through which the cleaning container is connected to the side of the first opening of the filtration apparatus and the waste fluid container is connected to the side of the second opening of the filtration apparatus.

By using the microorganism recovering apparatus configured as such, the filtration apparatus can be cleaned, and as a result of cleaning of the filtration apparatus, microorganisms can be recovered with high purity.

(Clause 13)

The microorganism recovering apparatus described in Clause 12 may further include a first switch that switches connection to the first opening to the sample container, the recovering container, or the cleaning container and a second switch that switches connection to the second opening to the waste fluid container or the recovering fluid container.

By using the microorganism recovering apparatus configured as such, switching from the first flow path to the third flow path and from the third flow path to the second flow path can be made simply by operating the first switch and the second switch. By automating the operation onto the first switch and the second switch, cleaning of the inside of the filtration apparatus and recovering of microorganisms can be automated.

(Clause 14)

In the microorganism recovering apparatus described in any one of Clauses 9 to 13, the liquid sample may contain blood cells. In this case, the sample container is a removal apparatus that removes blood cells. The sample container includes a first filter configured to permeate the blood cells and microorganisms smaller than the blood cells and allow the microorganisms to permeate faster than the blood cells and a second filter which is disposed on the downstream of the first filter and configured to selectively capture the blood cells by size and selectively permeate the microorganisms by size.

According to such a configuration, a unit operation of filtration can be performed on a liquid sample containing blood cells without performing any treatment thereon, and filtrate resulting from removal of blood cells from the liquid sample can be obtained by one unit operation. Furthermore, since the sample container that functions as the removal apparatus is connected to the filtration apparatus, by using such a microorganism recovering apparatus, operations to remove blood cells out of the liquid sample containing blood cells and even to filter out microorganisms can be performed by one unit operation.

(Clause 15)

The microorganism recovering apparatus described in Clause 11 or 13 may further include a housing that accommodates the sample container and the filtration apparatus and removably supports the recovering container and an enclosure where the first switch and the second switch are arranged, the housing being attachable to the enclosure. The housing is provided with at least a part of the first flow path and at least a part of the second flow path. The first flow path and the second flow path provided in the housing are each formed from a plastic tube. The first switch and the second switch switch connection by cutting off the first flow path or the second flow path by pinching and compressing the tube. The first switch and the second switch are positioned in the enclosure to pinch the tube when the housing is attached to the enclosure.

According to such a configuration, the first switch and the second switch each pinch and compress the tube. Therefore, in automating recovering of microorganisms, the first switch and the second switch that should be controlled by the controller can be separate from the tube (the first flow path and the second flow path) contaminated by a liquid sample. The first switch and the second switch are positioned in the enclosure to pinch the tube when the housing is attached to the enclosure. Therefore, a user can use the recovering apparatus simply by attaching or removing a non-reusable housing to or from the enclosure.

Though embodiments of the present invention have been described, it should be understood that the embodiments disclosed herein are illustrative and non-restrictive in every respect. The scope of the present invention is defined by the terms of the claims and is intended to include any modifications within the scope and meaning equivalent to the terms of the claims.

What is claimed is:

1. A microorganism recovering apparatus comprising:
   a sample container that receives a liquid sample;
   a filtration apparatus including a filter having a pore size smaller than a microorganism and a first opening and a second opening formed at positions opposed to each other with the filter being interposed;
   a waste fluid container that receives waste fluid;
   a recovering fluid container that receives recovering fluid;
   a recovering container that receives a solution to be recovered;
   a first flow path through which the sample container is connected to a side of the first opening of the filtration apparatus and the waste fluid container is connected to a side of the second opening of the filtration apparatus; and
   a second flow path through which the recovering fluid container is connected to a side of the second opening of the filtration apparatus and the recovering container is connected to the side of the first opening of the filtration apparatus.

2. The microorganism recovering apparatus according to claim 1, wherein
   the recovering fluid is a liquid culture medium to be used for culturing microorganisms.

3. The microorganism recovering apparatus according to claim 1, further comprising:
   a first switch that switches connection to the first opening to the sample container or the recovering container; and
   a second switch that switches connection to the second opening to the waste fluid container or the recovering fluid container.

4. The microorganism recovering apparatus according to claim 1, further comprising:
   a cleaning container that receives a cleaning solution; and
   a third flow path through which the cleaning container is connected to the side of the first opening of the filtration apparatus and the waste fluid container is connected to the side of the second opening of the filtration apparatus.

5. The microorganism recovering apparatus according to claim 4, further comprising:
   a first switch that switches connection to the first opening to the sample container, the recovering container, or the cleaning container; and
   a second switch that switches connection to the second opening to the waste fluid container or the recovering fluid container.

6. The microorganism recovering apparatus according to claim 1, wherein
   the liquid sample contains blood cells,
   the sample container is a removal apparatus that removes the blood cells,
   the sample container includes
   a first filter configured to permeate the blood cells and microorganisms smaller than the blood cells and allow the microorganisms to permeate faster than the blood cells, and
   a second filter which is disposed on downstream of the first filter and configured to selectively capture the blood cells by size and selectively permeate the microorganisms by size.

7. The microorganism recovering apparatus according to claim 3, further comprising:
   a housing that accommodates the sample container and the filtration apparatus and removably supports the recovering container; and
   an enclosure where the first switch and the second switch are arranged, the housing being attachable to the enclosure, wherein
   the housing is provided with at least a part of the first flow path and at least a part of the second flow path,
   the first flow path and the second flow path provided in the housing are each formed from a plastic tube,
   the first switch and the second switch are configured to switch connection by cutting off the first flow path or the second flow path by pinching and compressing the plastic tube, and
   the first switch and the second switch are positioned in the enclosure to pinch the tube when the housing is attached to the enclosure.

8. A microorganism recovering apparatus comprising:
   a filtration apparatus including a filter having a pore size smaller than a microorganism and a first opening and a second opening formed at positions opposed to each other with the filter being interposed;
a sample container that receives a liquid sample and is connectable to the first opening of the filtration apparatus;
a waste fluid container that receives waste fluid and is connectable to the second opening of the filtration apparatus;
a recovering fluid container that receives recovering fluid and is connectable to the second opening of the filtration apparatus;
a recovering container that receives a solution to be recovered and is connectable to the first opening of the filtration apparatus, wherein
a first flow path is formed by the sample container being connected to the first opening of the filtration apparatus and the waste fluid container being connected to the second opening of the filtration apparatus, the first flow path having a direction of flow through the filter from the first opening of the filtration apparatus to the second opening of the filtration apparatus, and
a second flow path is formed by the recovering fluid container being connected to the second opening of the filtration apparatus and the recovering container being connected to the first opening of the filtration apparatus, the second flow path having a direction of flow through the filter from the second opening of the filtration apparatus to the first opening of the filtration apparatus.

\* \* \* \* \*